United States Patent
Shi

(10) Patent No.: US 10,370,381 B2
(45) Date of Patent: Aug. 6, 2019

(54) INHIBITORS OF BRUTON'S TYROSINE KINASE

(71) Applicant: GILEAD SCIENCES, INC., Foster City, CA (US)

(72) Inventor: Bing Shi, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/903,285

(22) Filed: Feb. 23, 2018

(65) Prior Publication Data

US 2018/0251464 A1 Sep. 6, 2018

Related U.S. Application Data

(60) Provisional application No. 62/463,429, filed on Feb. 24, 2017.

(51) Int. Cl.
*C07D 487/04* (2006.01)
*C07D 473/34* (2006.01)

(52) U.S. Cl.
CPC ......... *C07D 487/04* (2013.01); *C07D 473/34* (2013.01); *C07B 2200/13* (2013.01)

(58) Field of Classification Search
CPC .. C07B 2200/13; C07D 473/34; C07D 487/04
See application file for complete search history.

(56) References Cited

U.S. PATENT DOCUMENTS

| | | | |
|---|---|---|---|
| 4,943,593 A | 7/1990 | Palfreyman et al. |
| 4,965,288 A | 10/1990 | Palfreyman et al. |
| 4,997,854 A | 3/1991 | Kagan et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,252,608 A | 10/1993 | Palfreyman et al. |
| 7,514,444 B2 | 4/2009 | Honigberg et al. |
| 8,450,321 B2 | 5/2013 | Mitchell et al. |
| 8,501,724 B1 | 8/2013 | Chen et al. |
| 8,557,803 B2 | 10/2013 | Yamamoto et al. |
| 8,940,725 B2 | 1/2015 | Yamamoto et al. |
| 8,940,893 B2 | 1/2015 | Bosanac et al. |
| 9,199,997 B2 | 12/2015 | Yamamoto et al. |
| 9,371,325 B2 | 6/2016 | Yamamoto et al. |
| 9,550,835 B2 | 1/2017 | Ono et al. |

| | | |
|---|---|---|
| 2004/0248871 A1 | 12/2004 | Farjanel et al. |
| 2009/0142345 A1 | 6/2009 | Saton et al. |
| 2011/0287011 A1 | 11/2011 | Gurney et al. |
| 2014/0142099 A1 | 5/2014 | Owens |
| 2015/0175616 A1 | 6/2015 | Blomgren et al. |

FOREIGN PATENT DOCUMENTS

| | | | |
|---|---|---|---|
| EP | 2 786 996 | * 10/2014 | .......... C07D 473/34 |
| EP | 2786996 A1 | 10/2014 | |
| WO | 2005/113556 A1 | 1/2005 | |
| WO | 2008/121742 A2 | 10/2008 | |
| WO | 2009/017833 A2 | 2/2009 | |
| WO | 2009/035791 A1 | 3/2009 | |
| WO | 2011/008709 A1 | 1/2011 | |
| WO | 2011/0975513 A1 | 8/2011 | |
| WO | 2012/027721 A2 | 3/2012 | |
| WO | 2013/010380 A1 | 1/2013 | |
| WO | 2013/010868 A1 | 1/2013 | |
| WO | 2013/010869 A1 | 1/2013 | |
| WO | 2013/034933 A1 | 3/2013 | |
| WO | 2013/052699 A2 | 4/2013 | |
| WO | 2013/112741 A1 | 8/2013 | |
| WO | 2013/116562 A1 | 8/2013 | |
| WO | 2014/047624 A1 | 3/2014 | |
| WO | 2014/100765 A1 | 6/2014 | |
| WO | 2014/100767 A1 | 6/2014 | |
| WO | 2014/201409 A1 | 12/2014 | |
| WO | 2015/002894 A1 | 1/2015 | |
| WO | 2013/027802 A1 | 3/2015 | |
| WO | 2015/048689 A1 | 4/2015 | |
| WO | 2015181633 A2 | 12/2015 | |
| WO | WO 2015/181633 | * 12/2015 | |

OTHER PUBLICATIONS

Berge, et al., Pharmaceutical Salts, J. of Pharm. Sciences (1977). (Year: 1977).*
Foster, "Deuterium Isotope Effects in Studies of Drug Metabolism", Trends Pharmacal. Sci. 5(12):524 (1984).
Poste et al., "Lipid Vesicles as Carriers for Introducing Biologically Active Materials into Cells", Methods in Cell Biology (Prescott (Ed.)), vol. XIV, p. 33 (1976).
International Search Report for International Application No. PCT/US2018/019422 dated Jul. 16, 2018 (6 pages).
Written Opinion for International Application No. PCT/US2018/019422 dated Jul. 16, 2018 (10 pages).

* cited by examiner

*Primary Examiner* — Erich A Leeser
(74) *Attorney, Agent, or Firm* — Venable LLP

(57) ABSTRACT

Provided are forms of 6-amino-9-[(3R)-1-(2-butynoyl)-3-pyrrolidinyl]-7-(4-phenoxyphenyl)-7,9-dihydro-8H-purin-8-one, compositions thereof, methods for their preparation, and methods for their use.

32 Claims, 28 Drawing Sheets

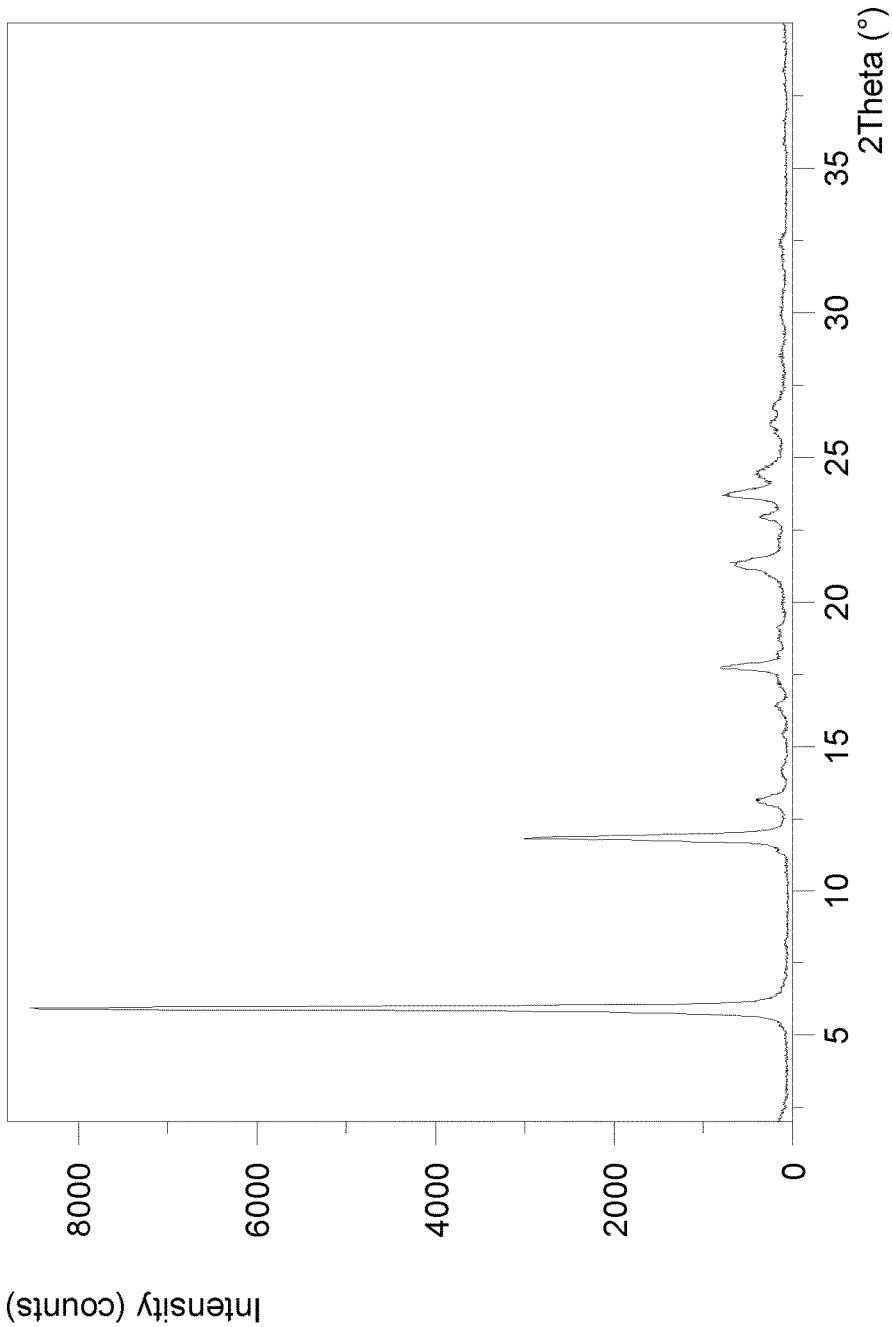

INHIBITORS OF BRUTON'S TYROSINE KINASE

CROSS-REFERENCE TO RELATED APPLICATION

The applicant claims the benefit under Title 35, United States Code, Section 119(e) of U.S. Provisional Application Ser. No. 62/463,429 filed on Feb. 24, 2017, the disclosure of which is hereby incorporated by reference in its entirety.

FIELD

The present application relates generally to therapeutics and compositions for treating diseases, and more specifically to Bruton's Tyrosine Kinase (BTK) inhibitors.

BACKGROUND

BTK is a member of the Tec family of kinases and is involved in signal transduction in B cells and the activation of mast cells. Several compounds have been identified as BTK inhibitors. Examples are disclosed in U.S. Pat. Nos. 7,514,444, 8,501,724, 8,557,803, 8,940,725, 8,940,893, 9,199,997, and 9,371,325; U.S. Pub. Patent App. No. 2014/0142099; PCT Pub. Nos. WO 2008/121742, WO 2013/010380, WO 2013/010868, WO 2013/010869, WO 2015/002894, and WO 2015/048689. Some BTK inhibitors are evaluated as potential therapeutics of, for example, autoimmune diseases and cancers.

There is a need for developing therapeutic agents that inhibit BTK to treat diseases, disorders, or conditions that are mediated by BTK.

BRIEF SUMMARY

In one aspect, provided herein are salt and co-crystal forms of Compound (I) having the following structure:

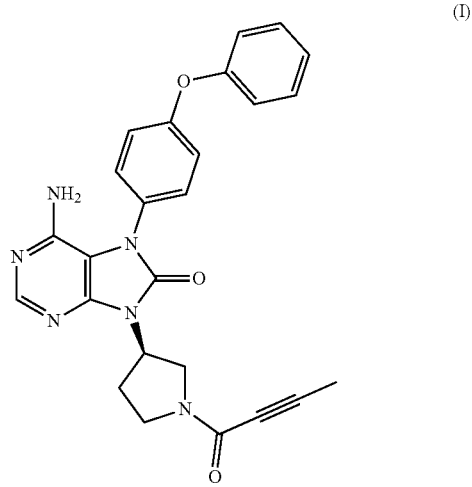 [SMILES: CC#CC(=O)N1CC[C@@H](n2c(=O)n(-c3ccc(Oc4ccccc4)cc3)c3c(N)ncnc32)C1]

(I)

In some aspects, provided herein are hemisulfate, oxalate, hemiedisylate, edisylate, heminapadisylate, fumarate, or succinate of Compound (I). In certain aspects, provided herein are hemisulfate, oxalate, hemiedisylate, edisylate, heminapadisylate, fumarate, or succinate of Compound (I) in salt or co-crystal forms.

In another aspect, provided are pharmaceutical compositions comprising hemisulfate, oxalate, hemiedisylate, edisylate, heminapadisylate, fumarate, or succinate of Compound (I) and one or more pharmaceutically acceptable carriers or excipients. Provided are also articles of manufacture and unit dosage forms comprising hemisulfate, oxalate, hemiedisylate, edisylate, heminapadisylate, fumarate, or succinate of Compound (I). Provided are also kits comprising hemisulfate, oxalate, hemiedisylate, edisylate, heminapadisylate, fumarate, or succinate of Compound (I) described herein and instructions for use (e.g., instructions for use in BTK-mediated disorder, such as an autoimmune disease or a cancer).

In one variation, provided are methods of treating a BTK-mediated disorder in a human in need thereof, comprising administering to the human hemisulfate, oxalate, hemiedisylate, edisylate, heminapadisylate, fumarate, or succinate of Compound (I) or compositions (including pharmaceutical compositions) thereof. The BTK-mediated disorder, in some embodiments, is an autoimmune disease or a cancer.

Also provided are uses of hemisulfate, oxalate, hemiedisylate, edisylate, heminapadisylate, fumarate, or succinate of Compound (I) or compositions (including pharmaceutical compositions) thereof in the manufacture of medicaments for the treatment of a disease responsive to inhibition of BTK activity, such as an autoimmune disease or a cancer.

Further provided are the methods of making hemisulfate, oxalate, hemiedisylate, edisylate, heminapadisylate, fumarate, or succinate of Compound (I). Moreover, provided are the methods of producing compositions comprising hemisulfate, oxalate, hemiedisylate, edisylate, heminapadisylate, fumarate, or succinate of Compound (I).

The methods of making hemisulfate, oxalate, hemiedisylate, edisylate, heminapadisylate, fumarate, or succinate of Compound (I) comprise combining a suitable acid and Compound (I) with a suitable solvent or a suitable mixture of solvents. Suitable acids may include, but are not limited to, sulfuric acid, oxalic acid, ethane-1,2-disulfonic acid, naphthalene-1,5-disulfonic acid, fumaric acid and succinic acid. Suitable solvents may include, but are not limited to, methanol, ethanol, water, isopropyl acetate, ethyl acetate, methyl tert-butyl ether, n-heptane, acetonitrile, acetone, 2-methyltetrahydrofuran, tetrahydrofuran, methyl isobutyl ketone, methyl ethyl ketone, dichloromethane, 2-propanol, 1-propanol, 1-butanol, and any mixtures thereof. Also provided are hemisulfate, oxalate, hemiedisylate, edisylate, heminapadisylate, fumarate, or succinate of Compound (I) obtained by the processes (e.g. methods of making) detailed herein.

DESCRIPTION OF THE FIGURES

The present disclosure can be best understood by references to the following description taken in conjunction with the accompanying figures.

FIGS. 3A-3D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) hemiedisylate.

DETAILED DESCRIPTION

Figure 1A:
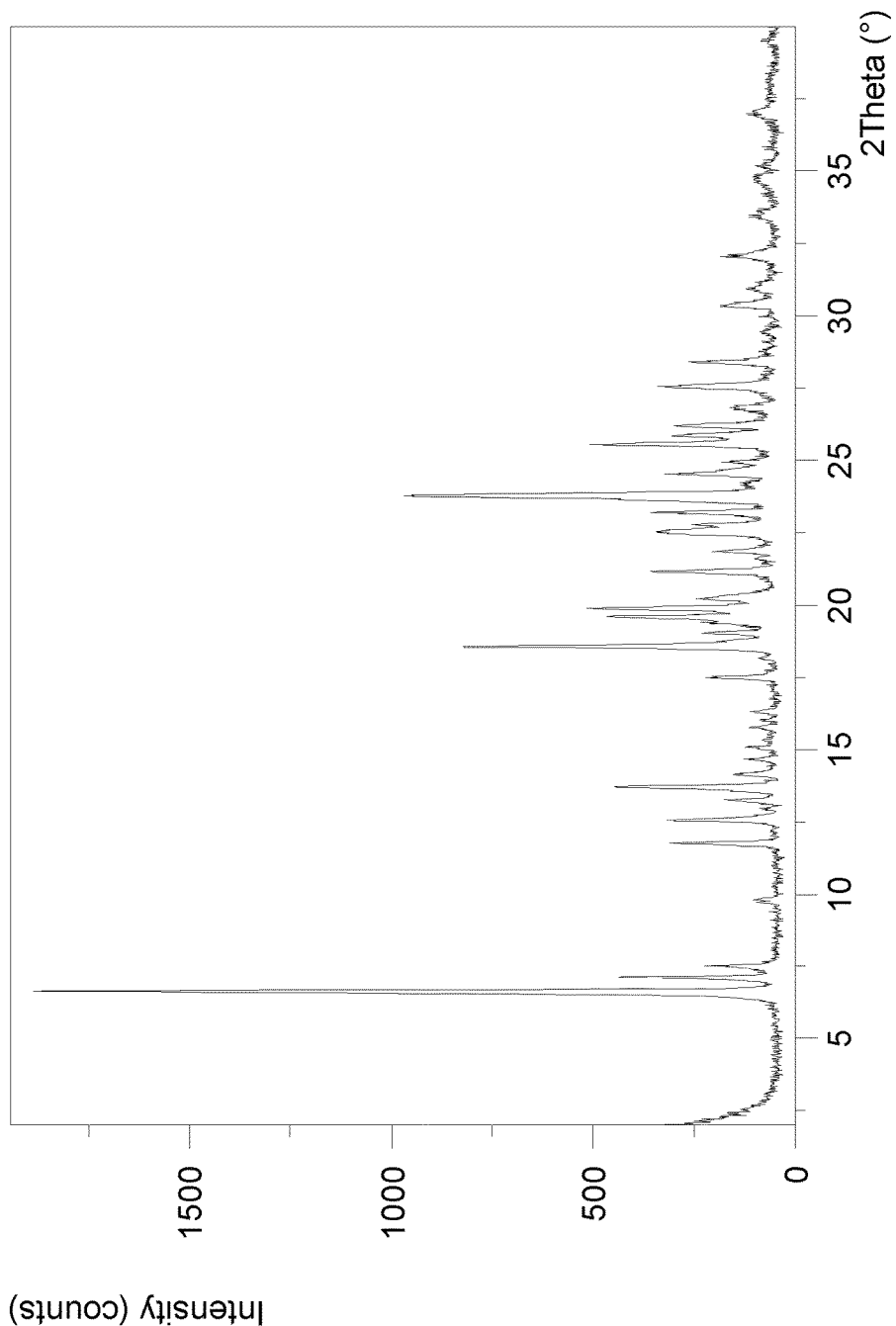
FIG. 1A-1D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) hemisulfate.

The following description is presented to enable a person of ordinary skill in the art to make and use the various embodiments. Descriptions of specific compounds, methods, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

As used in the present application, the following words and phrases are generally intended to have the meanings as set forth below, except to the extent that the context in which they are used indicates otherwise. The term "about" includes and describes the value or parameter per se. For example, "about x" includes and describes "x" per se. In certain embodiment, the term "about" when used in association with a measurement, or used to modify a value, a unit, a constant, or a range of values, refers to variations of +/−1-10%. In some embodiments, the term "about" when used in association with a measurement, or used to modify a value, a unit, a constant, or a range of values, refers to variations of +/−5%. In some embodiments, the term "about" when used in association with a measurement, or used to modify a value, a unit, a constant, or a range of values, refers to variations of +/−10%. The term "between" includes and describes the value or parameter per se. For example, "between x and y" includes and describes "x" and "y" per se.

The term "and/or" includes subject matter in the alternative as well as subject matter in combination. For instance, "x, and/or y", includes "x or y" and "x and y".

A compound of a given formula is intended to encompass the compounds of the disclosure, and the salts, esters, isomers, tautomers, solvates, isotopes, hydrates, forms (including polymorphic, pseudopolymorphic, crystal, or co-crystal forms) and prodrugs of such compounds. Additionally, the compounds of the disclosure may possess one or more asymmetric centers, and can be produced as a racemic mixture, a non-racemic mixture, a mixture of diastereoisomers or as individual enantiomers or diastereoisomers. The number of stereoisomers present in any given compound of a given formula depends upon the number of asymmetric centers present (there are 2n stereoisomers possible where n is the number of asymmetric centers). The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated. Compounds of the present disclosure include separable rotational isomers, or atropisomers.

"Isomers" are different compounds that have the same molecular formula. Isomers include stereoisomers, enantiomers and diastereoisomers. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other.

The absolute stereochemistry is specified according to the Cahn Ingold Prelog R S system. When the compound is a pure enantiomer, the stereochemistry at each chiral carbon maybe specified by either R or S. Resolved compounds whose absolute configuration is unknown are designated (+) or (−) depending on the direction (dextro- or laevorotary) that they rotate the plane of polarized light at the wavelength of the sodium D line.

"Tautomers" are structural isomers resulting from the migration of an atom or a functional group within the same organic molecule and lead to a change in one or more of its structural skeleton, electronic density distribution, and chemical properties. It is understood that compounds disclosed herein includes tautomeric forms although not necessarily explicitly shown. In one example, purine may be represented by any of the following tautomers:

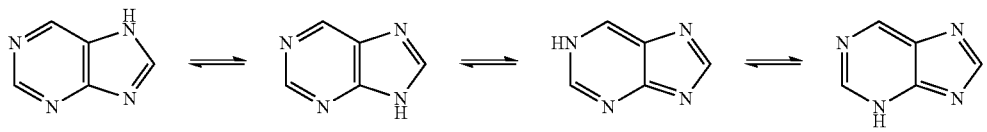 [SMILES: c1ncc2[nH]cnc2n1 ; c1ncc2nc[nH]c2n1 ; c1nc2c[nH]cnc-2n1 ; c1nc2cnc[nH]c-2n1]

Accordingly, a reference to any one of the purine tautomers includes the other tautomeric forms.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereo isomers of it.

The term "solvate" refers to a complex formed by the combining of a compound of any formula as disclosed herein, and a solvent. The term "hydrate" refers to the complex formed by the combining of a compound of any formula disclosed herein, and water.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of any formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half-life of a compound of Formulae (I)-(III), when administered to a mammal. See, for example, Foster, "Deuterium Isotope Effects in Studies of Drug Metabolism", Trends Pharmacal. Sci. 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in a compound of any formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto. Base or acid addition salts can be prepared from inorganic and organic bases.

In some embodiments, a salt is a "pharmaceutically acceptable salt". A pharmaceutically acceptable salt of a given compound refers to salts that retain the biological effectiveness and properties of a given compound, and which are not biologically or otherwise undesirable. See: P. Heinrich Stahl and Camille G. Wermuth (Eds.) Pharmaceutical Salts: Properties, Selection, and Use (International Union of Pure and Applied Chemistry), Wiley-VCH; 2nd revise Edition (May 16, 2011).

Compounds described herein may be presented in the form of chemical structures or names. By way of example, Compound (I) may be named using ChemBioDraw Ultra 10.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC).

Forms of Compound (I)

The present application provides the compounds inhibit BTK activities, suitable as BTK inhibitors. In one aspect, the BTK inhibitor is a salt or form of Compound (I) having the following structure:

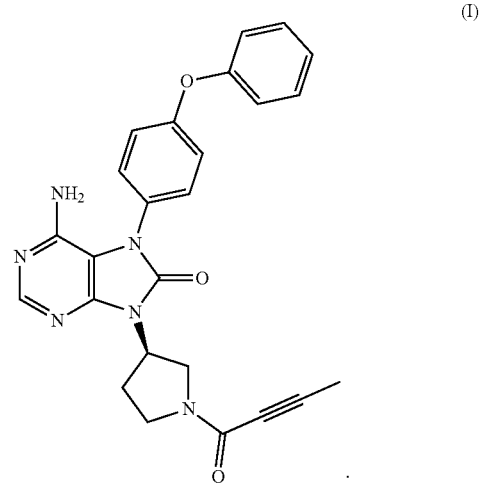 [SMILES: CC#CC(=O)N1CC[C@@H](n2c(=O)n(-c3ccc(Oc4ccccc4)cc3)c3c(N)ncnc32)C1]

(I)

Compound (I) may be also represented as 6-amino-9-[(3R)-1-(2-butynoyl)-3-pyrrolidinyl]-7-(4-phenoxyphenyl)-7,9-dihydro-8H-purin-8-one.

In other aspect, the BTK inhibitor is a salt or co-crystal form of Compound (I). In some embodiment, the BTK inhibitor is hemisulfate, oxalate, hemiedisylate, edisylate, heminapadisylate, fumarate, or succinate of Compound (I). The hemisulfate, oxalate, hemiedisylate, edisylate, heminapadisylate, fumarate, and succinate of Compound (I) may be presented in any forms, including salt or co-crystal forms. These salt or co-crystal forms may be characterized by a variety of solid state analytical data, including, for example, X-ray powder diffraction pattern (XRPD), differential scanning calorimetry (DSC), thermogravimetric analysis (TGA), and single crystal X-ray crystallography. One of skill in the art would recognize various techniques or methods that may be used to generate such characterization data. Unless otherwise stated, the XRPD patterns provided herein are generated by a powder X-ray diffractometer at room temperature.

A crystalline salt or co-crystal form of Compound (I) may provide the advantage of bioavailability and stability, suitable for use as an active ingredient in a pharmaceutical composition. 6-Amino-9-[(3R)-1-(2-butynoyl)-3-pyrrolidinyl]-7-(4-phenoxyphenyl)-7,9-dihydro-8H-purin-8-one disclosed in U.S. Pat. No. 8,557,803 is an example of a BTK inhibitor. Salts of BTK inhibitors are disclosed, for example, in U.S. Pat. Nos. 9,199,997, and 9,371,325. Each of these references is hereby incorporated herein by reference in its entirety. The salt or co-crystal form of Compound (I) hemisulfate, oxalate, hemiedisylate, edisylate, heminapadisylate, fumarate, or succinate may have similar or enhanced solubility compared to those of the salts disclosed in U.S. Pat. Nos. 9,199,997, and 9,371,325. In some embodiments, the terms of the salt or co-crystal forms of Compound (I), the compound of the present application, the compound described herein, BTK inhibitor of the present application, BTK inhibitor described here or variation thereof refer to Compound (I) hemisulfate, oxalate, hemiedisylate, edisylate, heminapadisylate, fumarate, or succinate, in salt or co-crystal form. Variations in the crystal structure of a pharmaceutical drug substance or active ingredient may affect the dissolution rate (which may affect bioavailability), manufacturability (e.g., ease of handling, ability to consistently prepare doses of known strength) and stability (e.g., thermal stability, shelf life) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline salt or co-crystal forms of Compound (I) provide the advantage of improving the manufacturing process of the active agent or the stability or storability of a drug product form of the compound or active ingredient, or having suitable bioavailability and/or stability as an active agent.

The use of certain acids has been found to produce different solid forms of Compound (I), including hemisulfate, oxalate, hemiedisylate, edisylate, heminapadisylate, fumarate and succinate forms, which may exhibit one or more favorable characteristics described herein, including but not being limited to bioavailability and stability. The processes for the preparation and characterization of the forms described herein. The term "substantially as shown in" when referring, for example, to an XRPD pattern, a DSC thermogram, a TGA thermogram, or a DVS graph includes a pattern, thermogram or graph that is not necessarily identical to those depicted herein, but that falls within the limits of experimental error or deviations when considered by one of ordinary skill in the art.

Compound (I) Hemisulfate

Figure 1B:
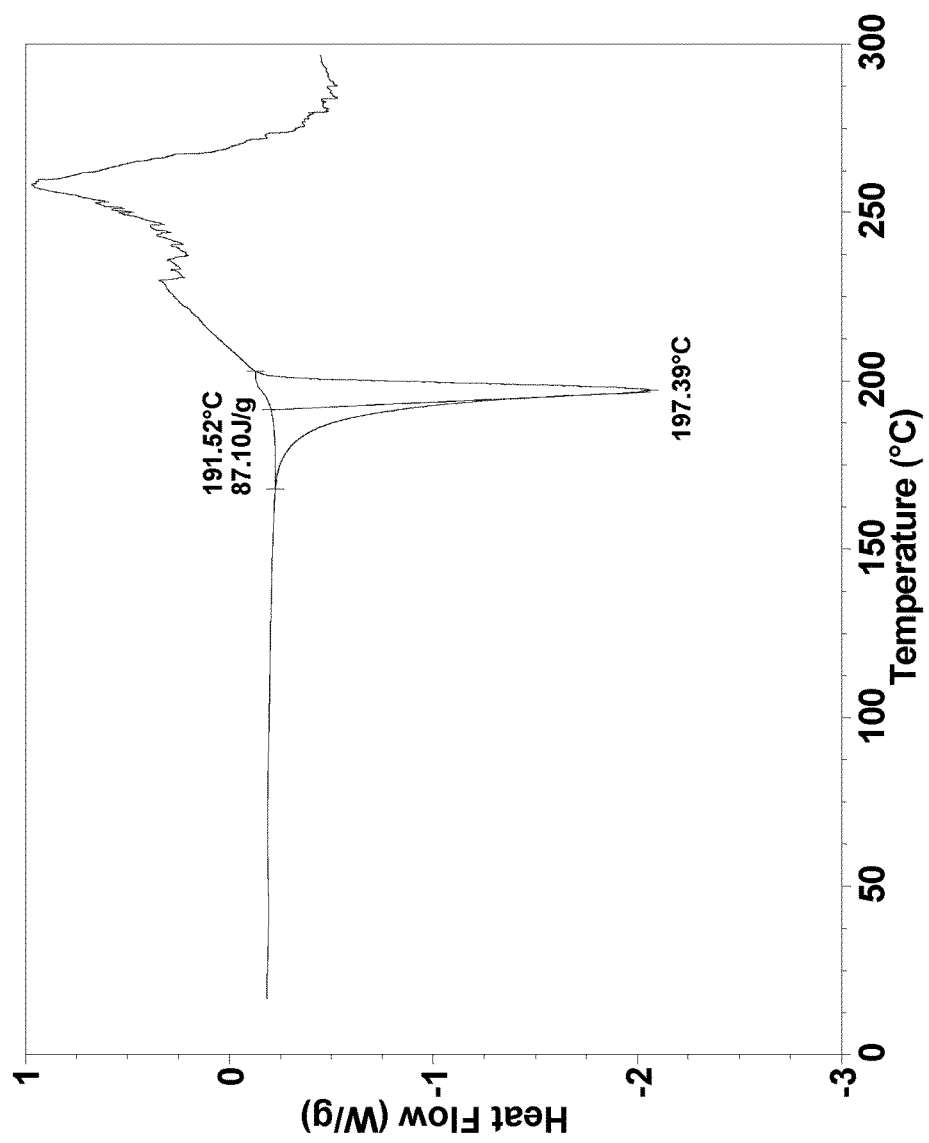
Figure 1C:
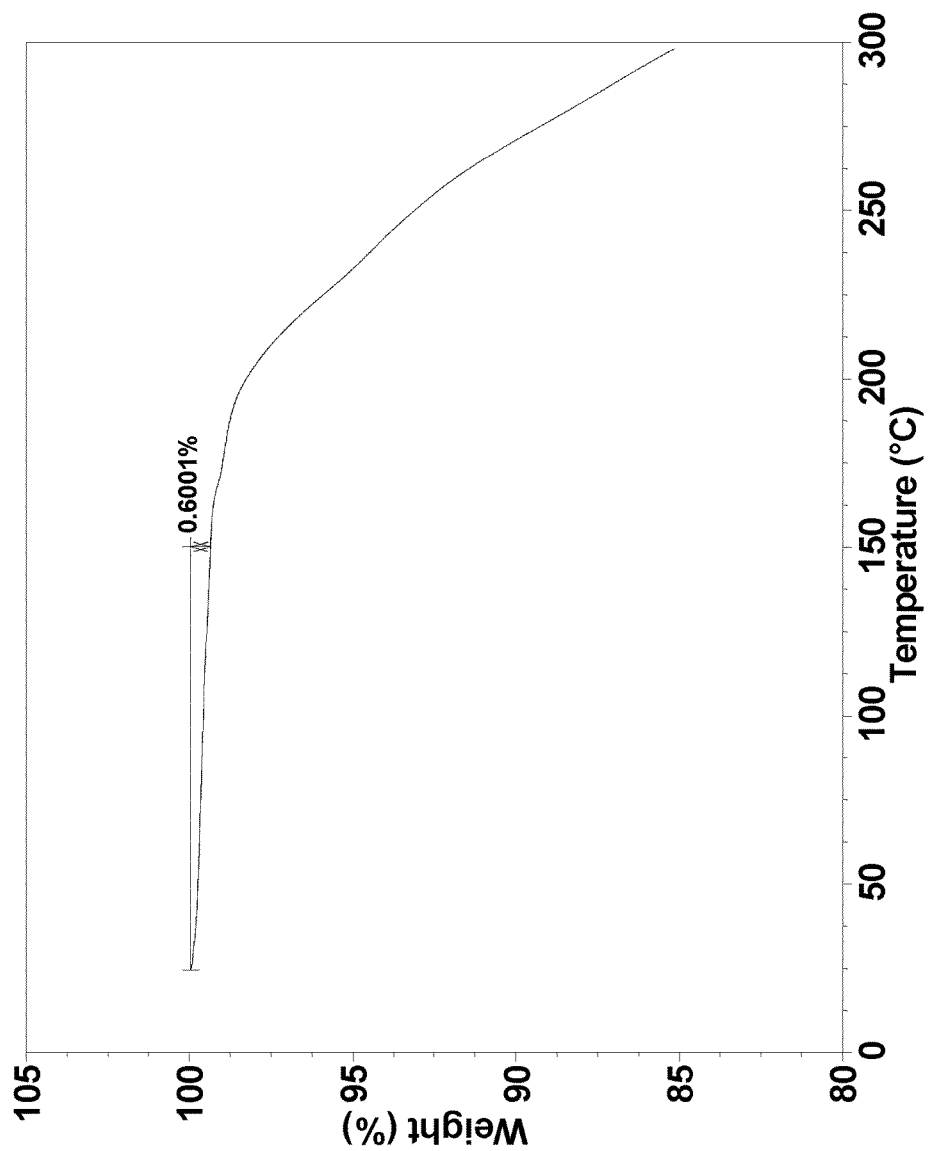
Figure 1D:
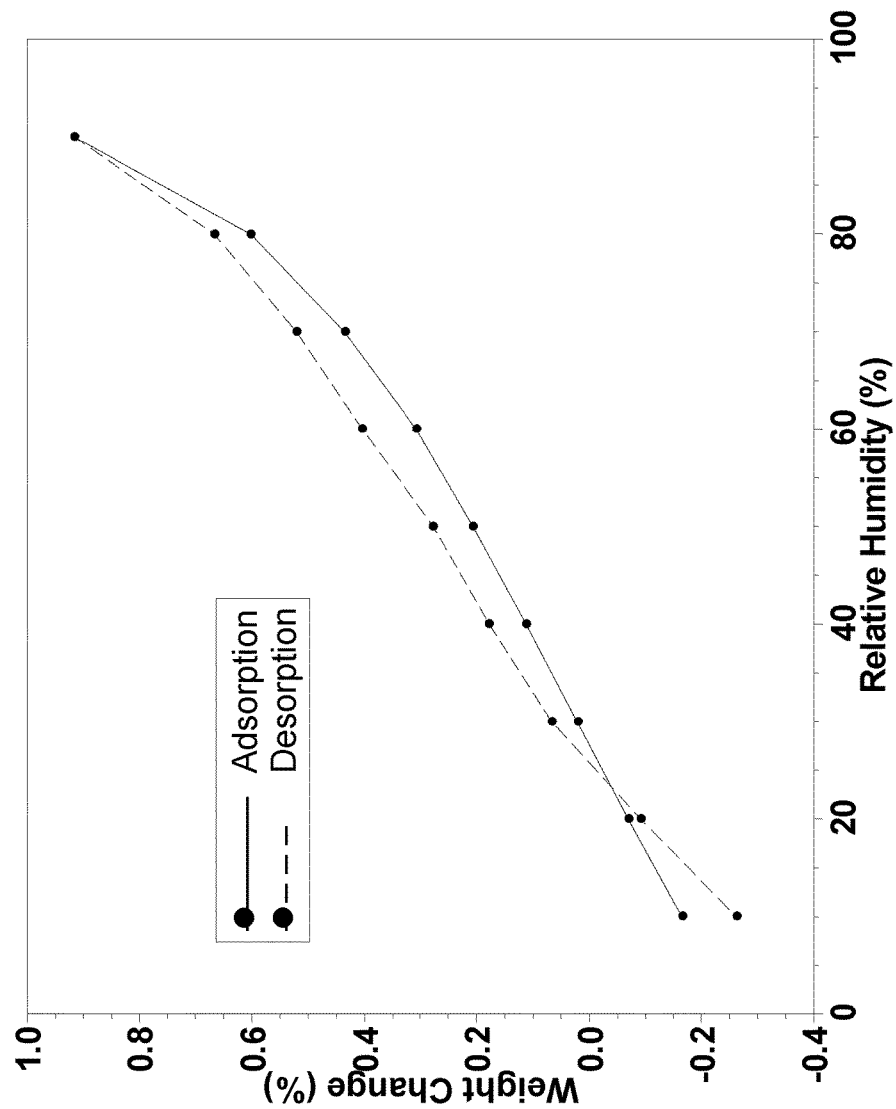

In one aspect, provided is Compound (I) hemisulfate, wherein the crystalline form exhibits an XRPD pattern substantially as shown in FIG. 1A. Compound (I) hemisulfate exhibits a differential scanning calorimetry (DSC) thermogram substantially as shown in FIG. 1B. Compound (I) hemisulfate exhibits a thermogravimetric analysis (TGA) thermogram substantially as shown in FIG. 1C. Compound (I) hemisulfate exhibits a dynamic vapor sorption (DVS) graph substantially as shown in FIG. 1D.

In some embodiments, Compound (I) hemisulfate has an XRPD pattern displaying at least two, at least three, at least four, or at least five of the degree 2θ-reflections with the greatest intensity as the XRPD pattern substantially as shown in FIG. 1A. It should be understood that relative intensities can vary depending on a number of factors, including sample preparation, mounting, and the instrument and analytical procedure and settings used to obtain the spectrum. As such, the peak assignments listed herein, including for Compound (I) hemisulfate, are intended to encompass variations of +/−0.2 degrees 2θ.

In certain embodiments, Compound (I) hemisulfate has an XRPD pattern comprising degree 2θ-reflections (+/−0.2 degrees 2θ) at 6.6, 18.6, and 23.7. In one embodiment, Compound (I) hemisulfate has an XRPD pattern comprising degree 2θ-reflections (+/−0.2 degrees 2θ) at 6.6, 7.1, 13.7, 18.6, and 23.7.

In certain embodiments, Compound (I) hemisulfate has a thermogravimetric analysis thermogram comprising a weight loss of about 0.6% from about 25° C. to about 150° C. In certain embodiments, Compound (I) hemisulfate has a differential scanning calorimetry curve comprising an endotherm at about 192° C. In certain embodiments, Compound (I) hemisulfate has a dynamic vapor sorption isotherm comprising a water uptake of about 1.2% from about 10% to about 90% RH at about 25° C. In some embodiments, Compound (I) hemisulfate has at least one, or both of the following properties:
  (a) an XRPD pattern substantially as shown in FIG. 1A;
  (b) a DSC thermogram substantially as shown in FIG. 1B.

Compound (I) Oxalate

Figure 2A:
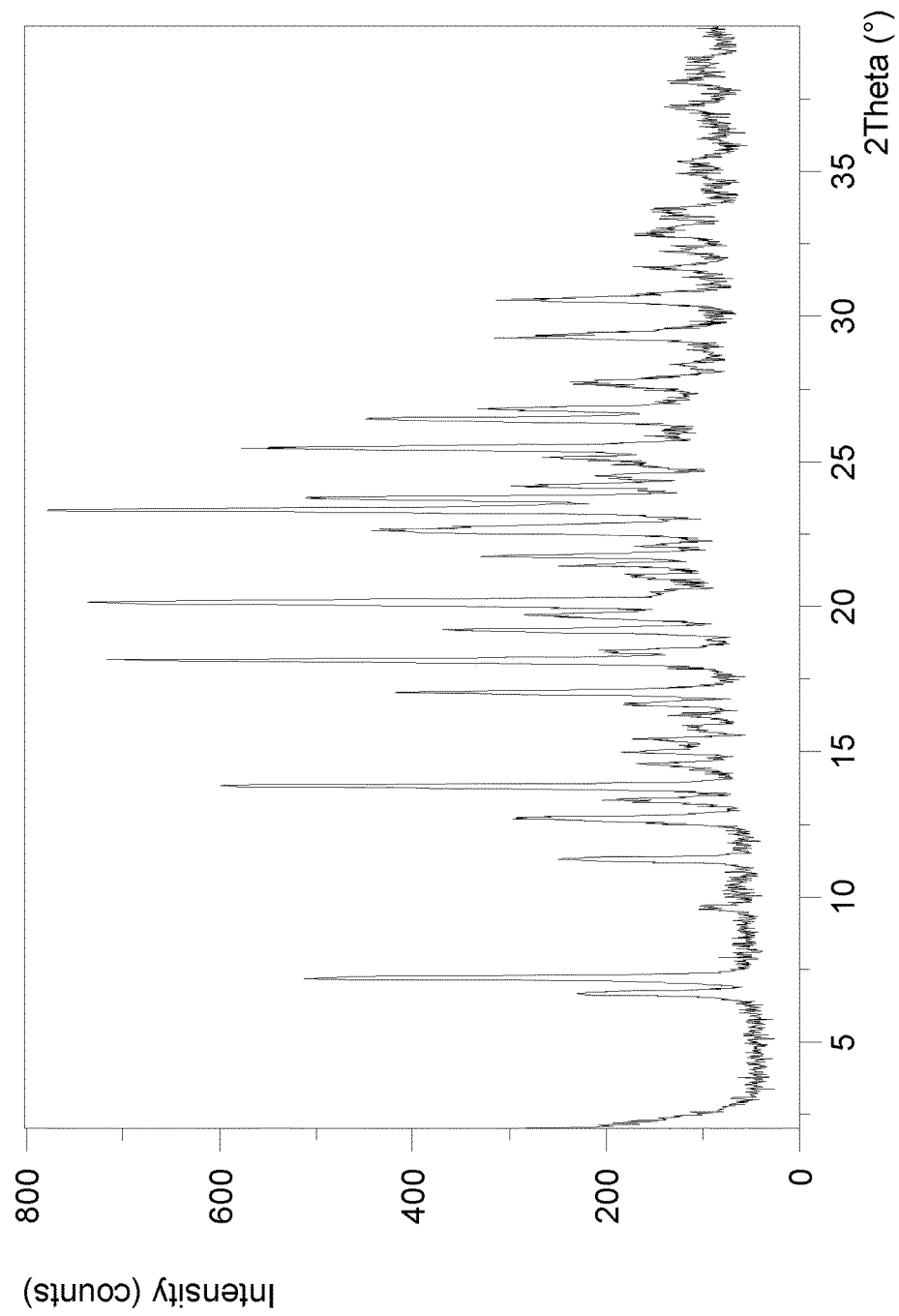
FIGS. 2A-2D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) oxalate.
Figure 2B:
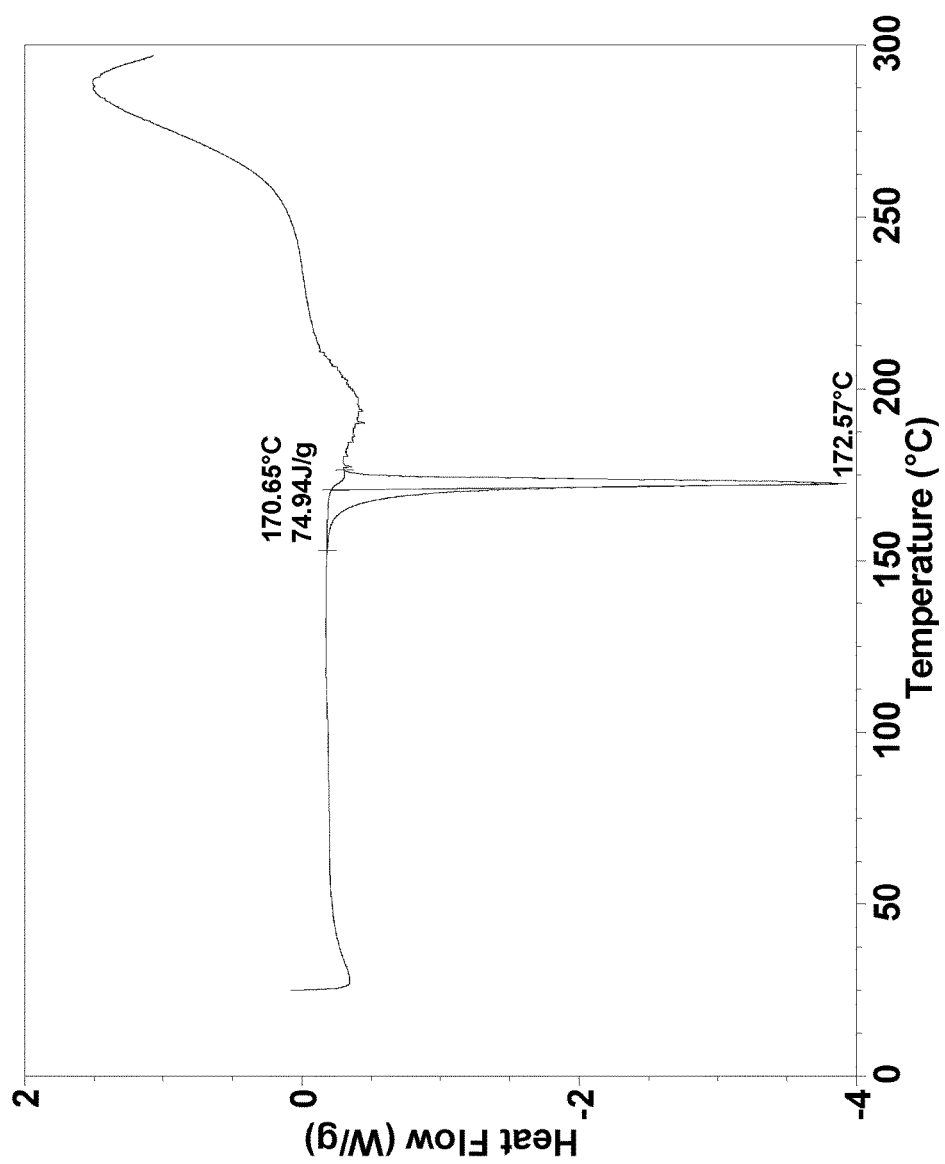
Figure 2C:
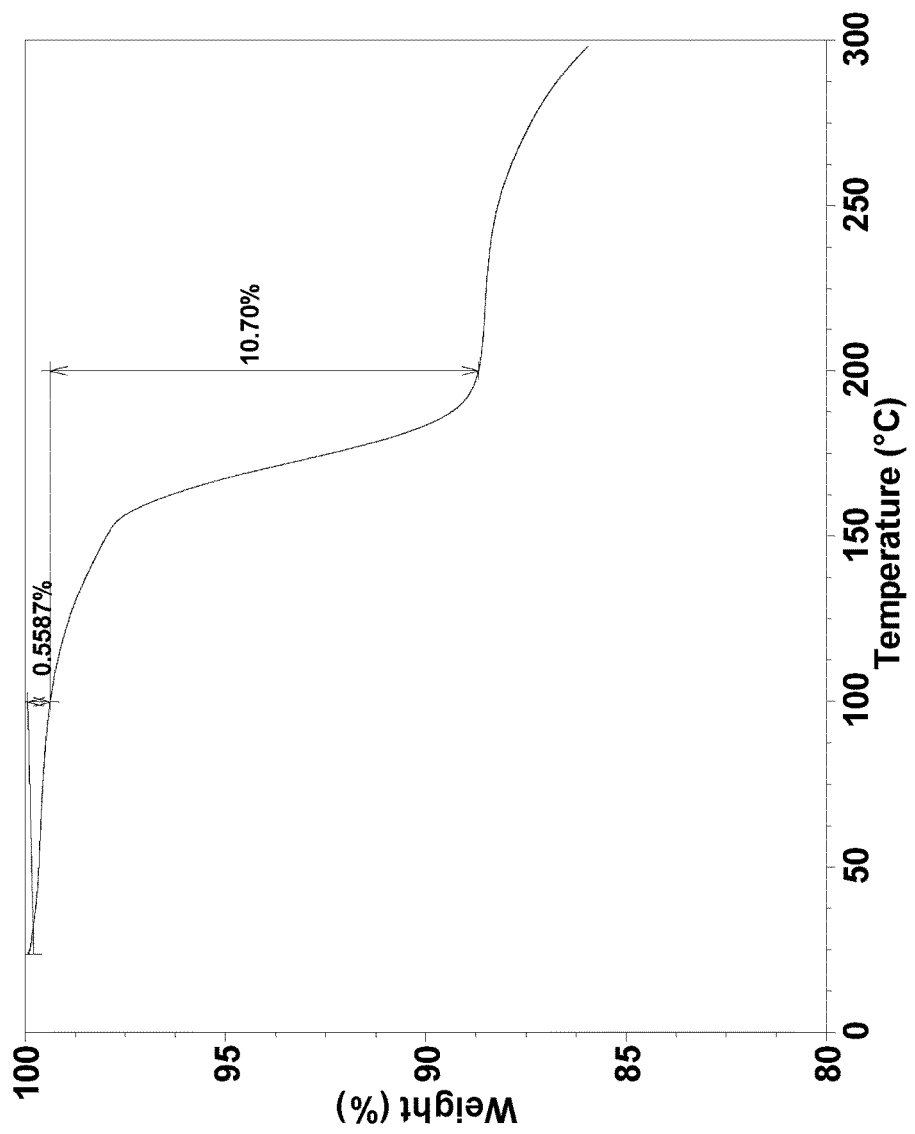
Figure 2D:
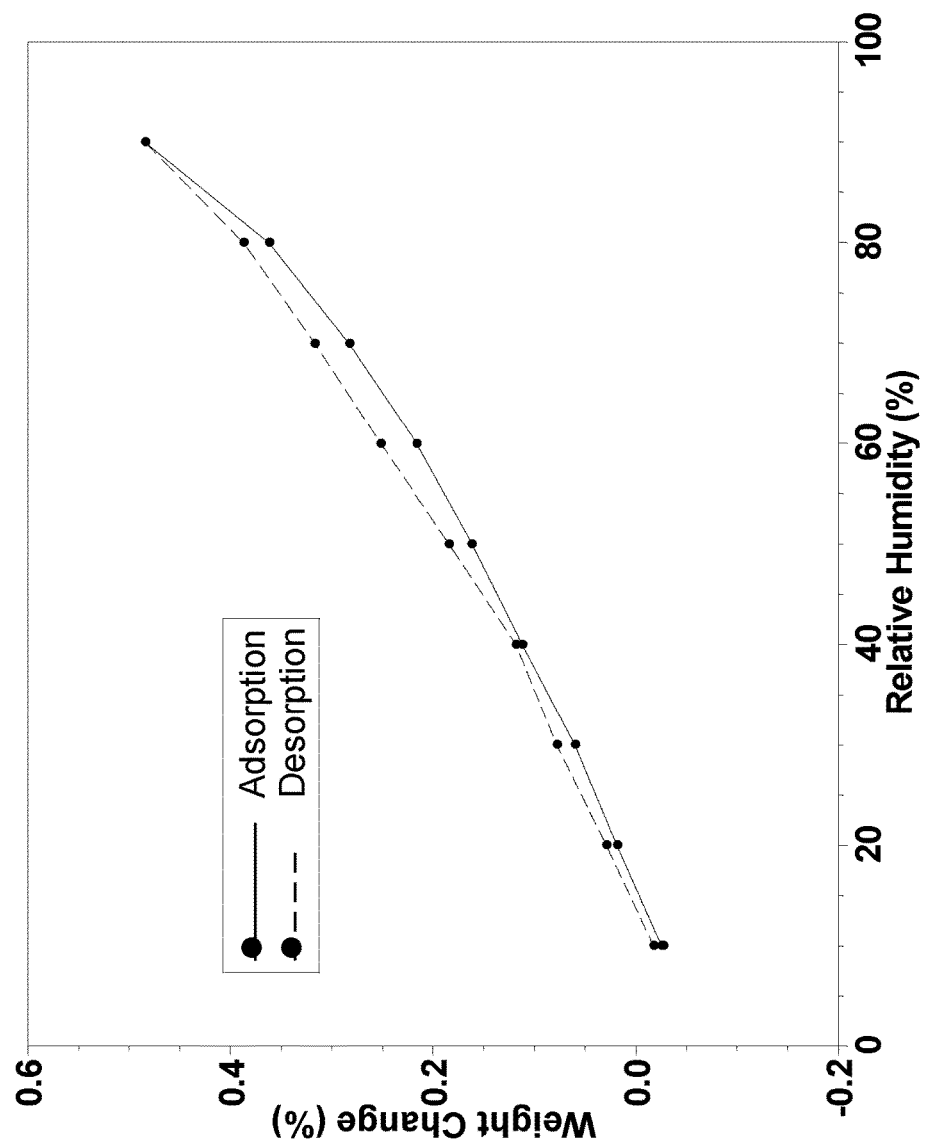

In one aspect, provided is Compound (I) oxalate, wherein the crystalline form exhibits an XRPD pattern substantially as shown in FIG. 2A. Compound (I) oxalate exhibits a differential scanning calorimetry (DSC) thermogram substantially as shown in FIG. 2B. Compound (I) oxalate exhibits a thermogravimetric analysis (TGA) thermogram substantially as shown in FIG. 2C. Compound (I) oxalate exhibits a dynamic vapor sorption (DVS) graph substantially as shown in FIG. 2D.

In some embodiments, Compound (I) oxalate has an XRPD pattern displaying at least two, at least three, at least four, or at least five of the degree 2θ-reflections with the greatest intensity as the XRPD pattern substantially as shown in FIG. 2A. It should be understood that relative intensities can vary depending on a number of factors including sample preparation, mounting, and the instrument and analytical procedure and settings used to obtain the spectrum. As such, the peak assignments listed herein, including for Compound (I) oxalate, are intended to encompass variations of +/−0.2 degrees 2θ.

In certain embodiments, Compound (I) oxalate has an XRPD pattern comprising degree 2θ-reflections (+/−0.2 degrees 2θ) at 7.2, 18.2, and 23.3. In one embodiment, Compound (I) oxalate has an XRPD pattern comprising degree 2θ-reflections (+/−0.2 degrees 2θ) at 7.2, 13.8, 18.2, 20.2, and 23.3.

In certain embodiments, Compound (I) oxalate has a thermogravimetric analysis thermogram comprising a weight loss of about 0.6% from about 25° C. to about 100° C. In one embodiment the thermogram of Compound (I) oxalate further comprises a weight loss of about 11% from about 100° C. to about 200° C. In certain embodiments, Compound (I) oxalate has a differential scanning calorimetry curve comprising an endotherm at about 171° C. In certain embodiments, Compound (I) oxalate has a dynamic vapor sorption isotherm comprising a water uptake of about 0.5% from about 10% to about 90% RH at about 25° C. In some embodiments, Compound (I) oxalate has at least one, or both of the following properties:
  (a) an XRPD pattern substantially as shown in FIG. 2A;
  (b) a DSC thermogram substantially as shown in FIG. 2B.

Compound (I) Hemiedisylate

Figure 3B:
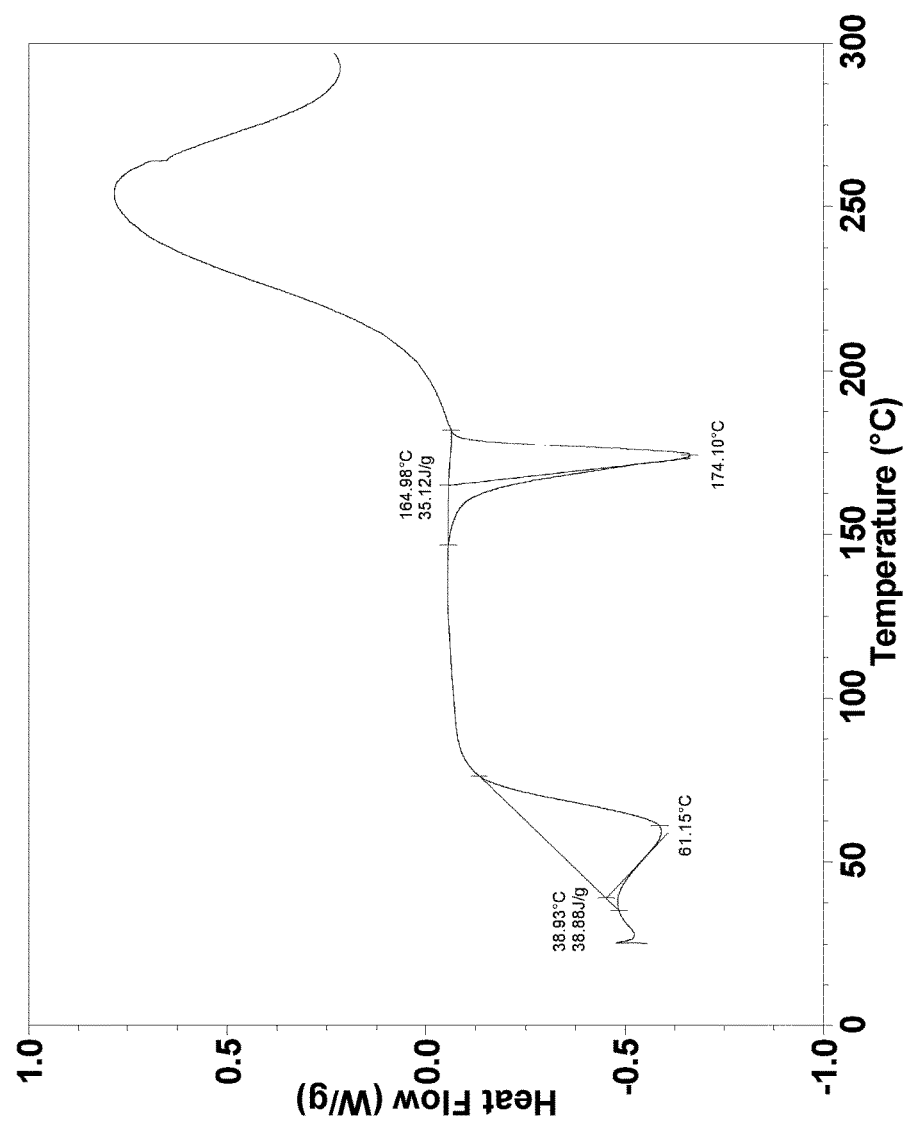
Figure 3C:
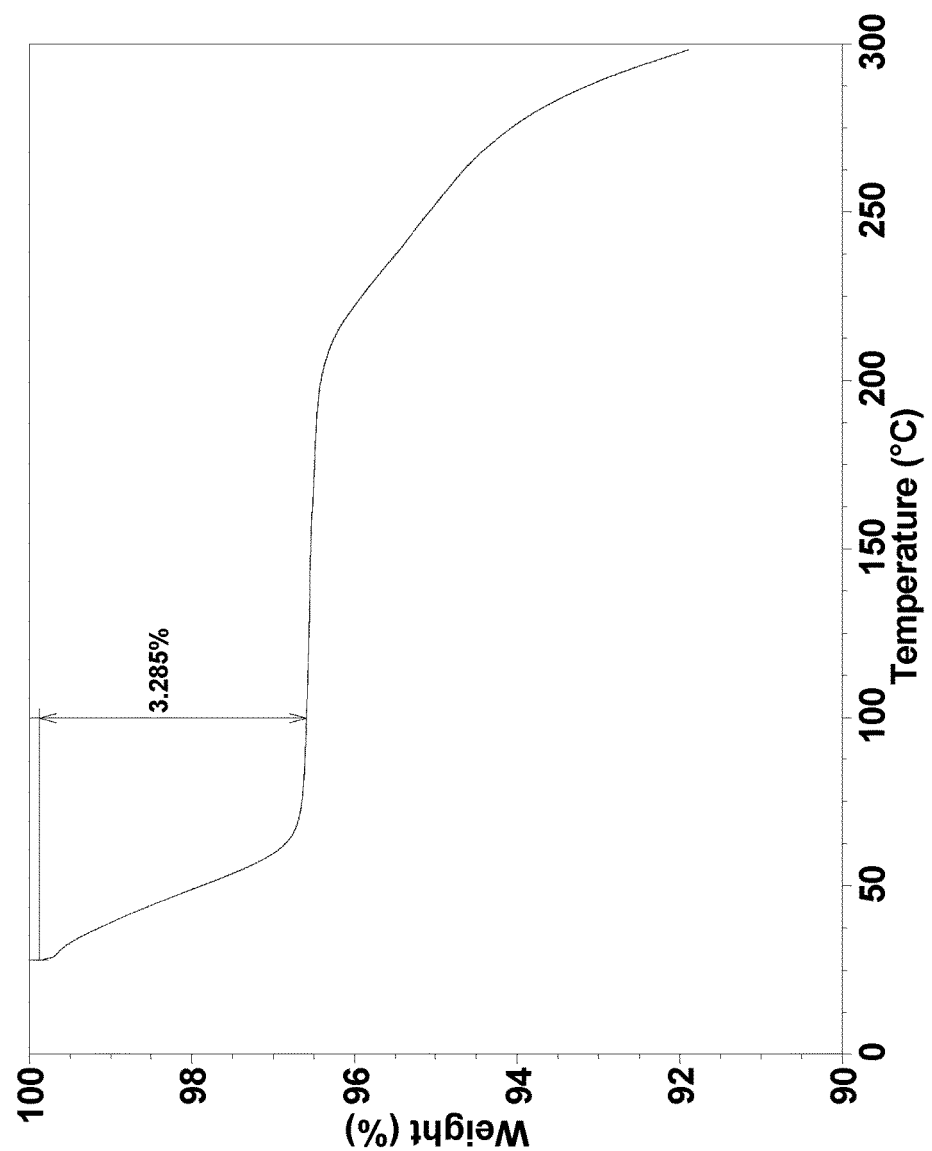
Figure 3D:
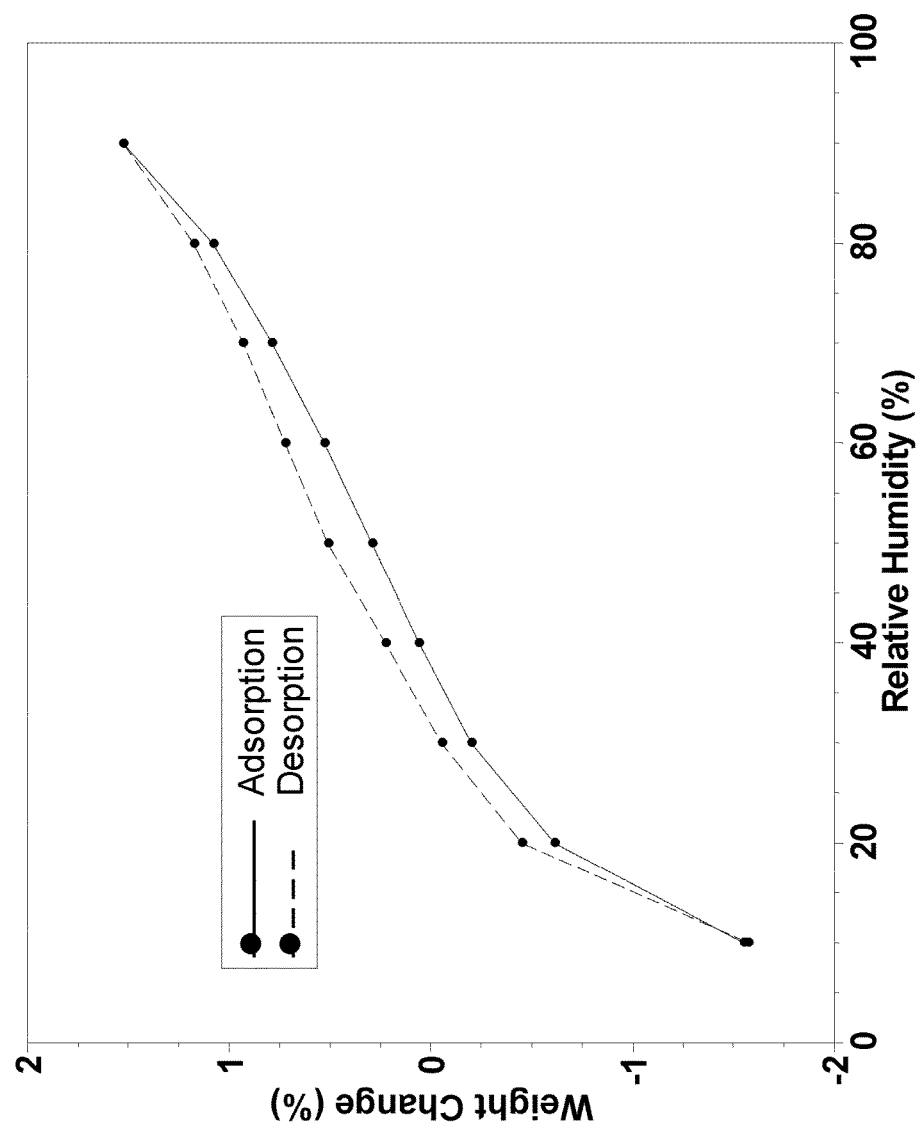

In one aspect, provided is Compound (I) hemiedisylate, wherein the crystalline form exhibits an XRPD pattern substantially as shown in FIG. 3A. Compound (I) hemiedisylate exhibits a differential scanning calorimetry (DSC) thermogram substantially as shown in FIG. 3B. Compound (I) hemiedisylate exhibits a thermogravimetric analysis (TGA) thermogram substantially as shown in FIG. 3C. Compound (I) hemiedisylate exhibits a dynamic vapor sorption (DVS) graph substantially as shown in FIG. 3D.

In some embodiments, Compound (I) hemiedisylate has an XRPD pattern displaying at least two, at least three, at least four, or at least five of the degree 2θ-reflections with the greatest intensity as the XRPD pattern substantially as shown in FIG. 3A. It should be understood that relative intensities can vary depending on a number of factors, including sample preparation, mounting, and the instrument and analytical procedure and settings used to obtain the spectrum. As such, the peak assignments listed herein, including for Compound (I) hemiedisylate, are intended to encompass variations of +/−0.2 degrees 2θ.

In certain embodiments, Compound (I) hemiedisylate has an XRPD pattern comprising degree 2θ-reflections (+/−0.2 degrees 2θ) at 5.9, 11.8, and 17.6. In one embodiment, Compound (I) hemiedisylate has an XRPD pattern comprising degree 2θ-reflections (+/−0.2 degrees 2θ) at 5.9, 11.8, 17.6, 21.2, and 23.6.

In certain embodiments, Compound (I) hemiedisylate has a thermogravimetric analysis thermogram comprising a weight loss of about 3.3% from about 25° C. to about 100° C. In certain embodiments, Compound (I) hemiedisylate has a differential scanning calorimetry curve comprising an endotherm at about 165° C. In certain embodiments, Compound (I) hemiedisylate has a dynamic vapor sorption isotherm comprising a water uptake of about 3% from about 10% to about 90% RH at about 25° C. In some embodiments, Compound (I) hemiedisylate has at least one, or both of the following properties:
  (a) an XRPD pattern substantially as shown in FIG. 3A;
  (b) a DSC thermogram substantially as shown in FIG. 3B.

Compound (I) Edisylate

Figure 4A:
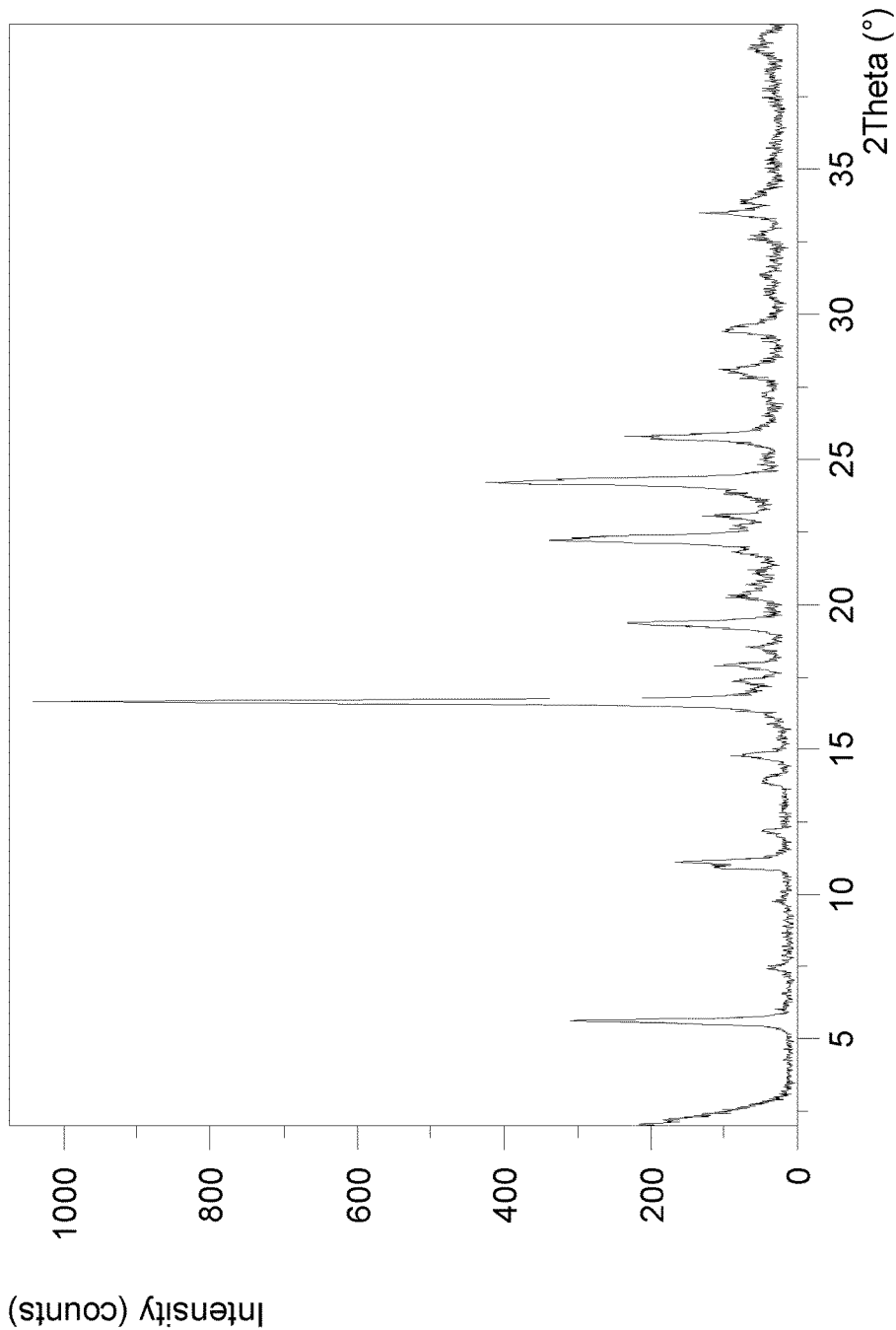
FIGS. 4A-4D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) edisylate.
Figure 4B:
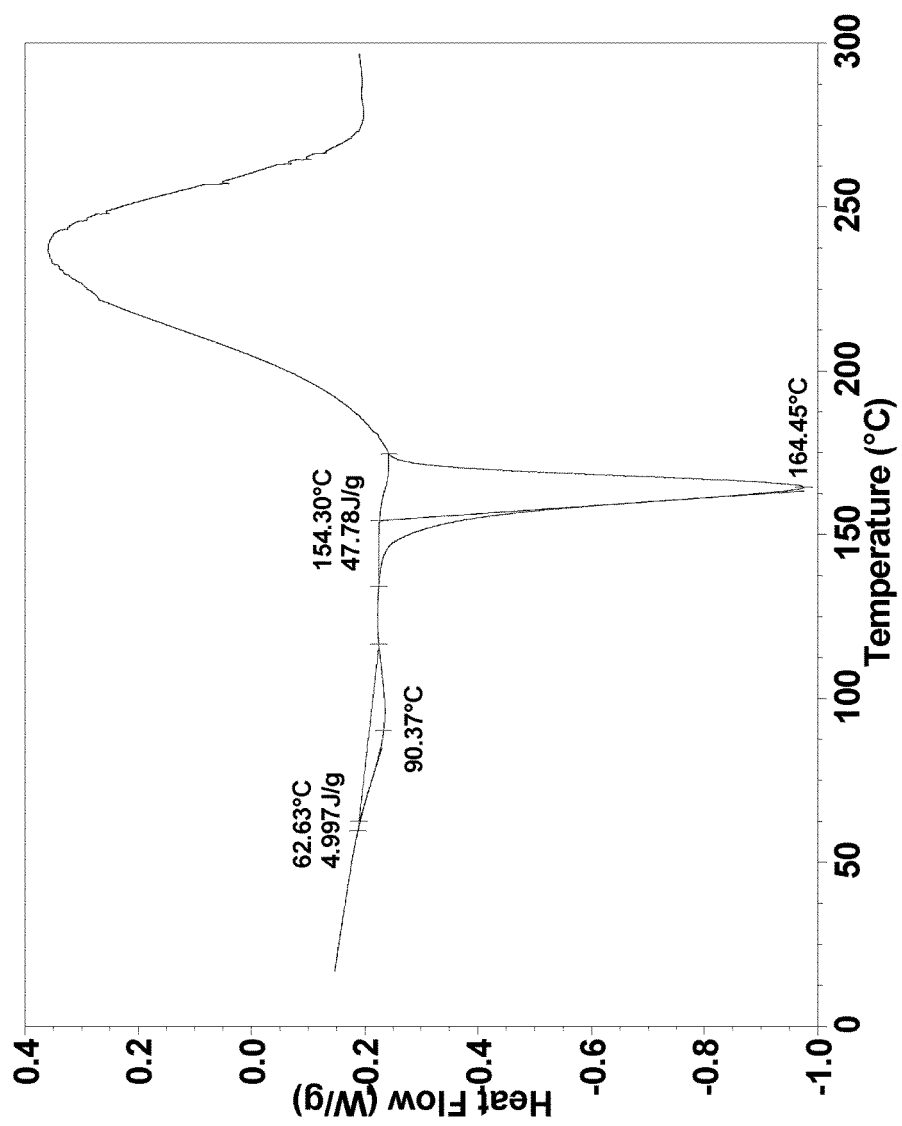
Figure 4C:
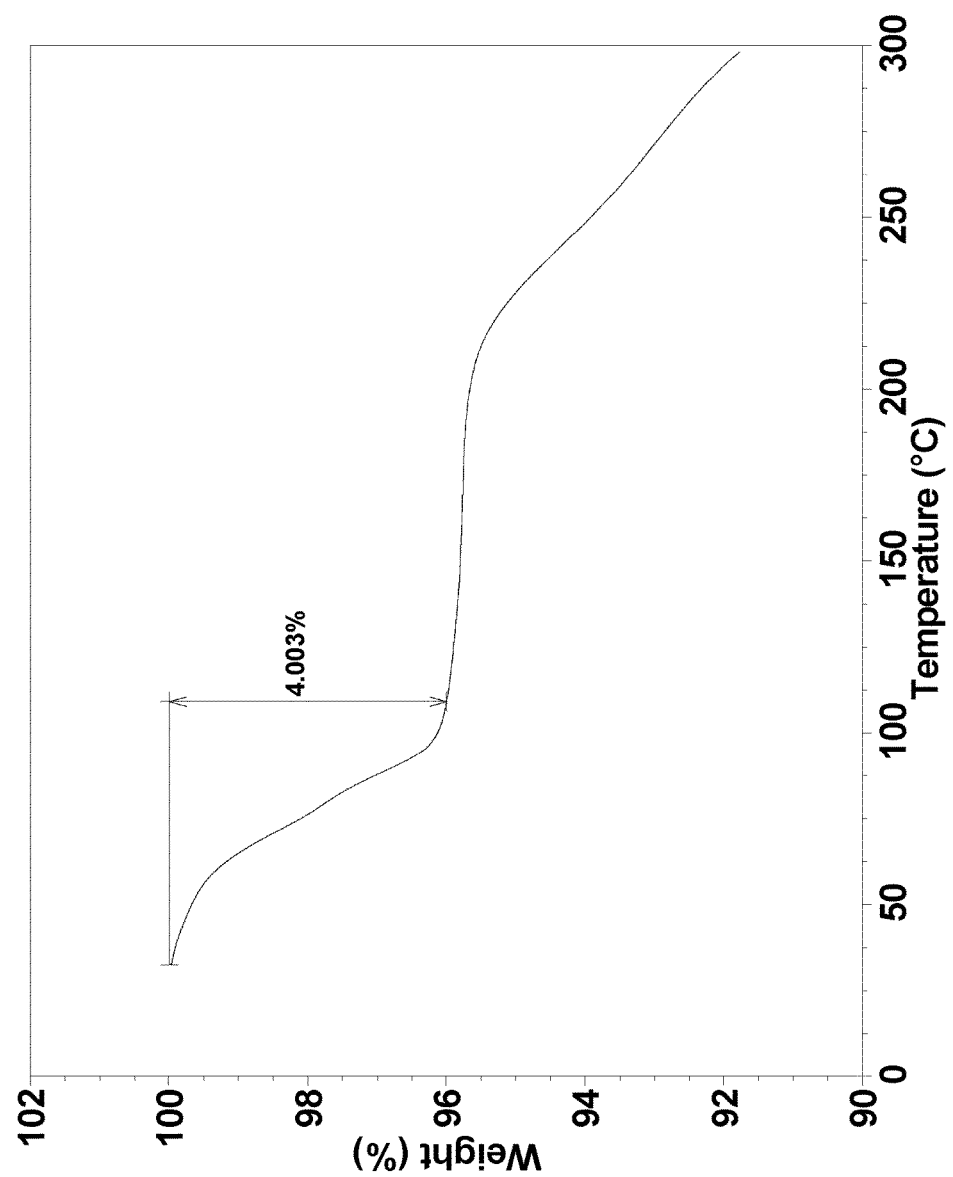
Figure 4D:
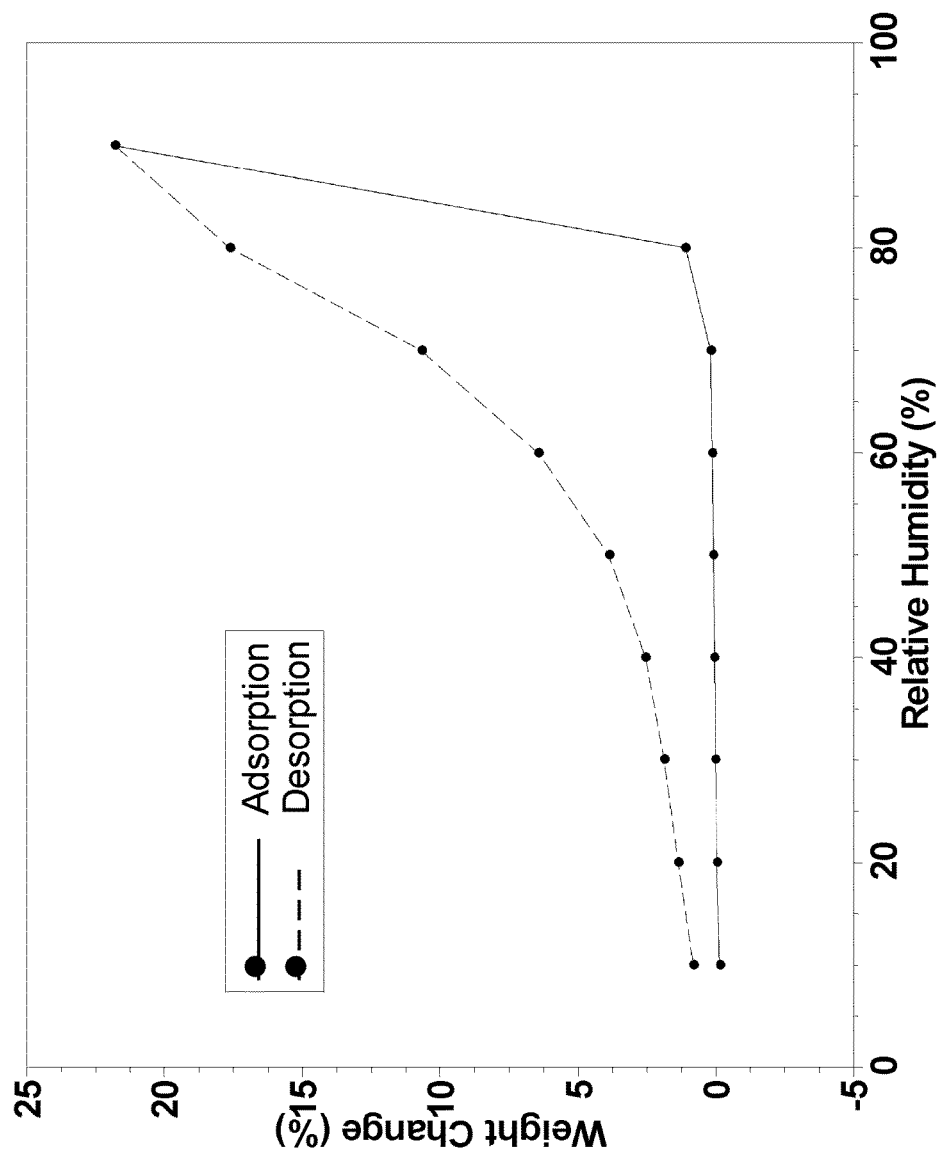

In one aspect, provided is Compound (I) edisylate, wherein the crystalline form exhibits an XRPD pattern substantially as shown in FIG. 4A. Compound (I) edisylate exhibits a differential scanning calorimetry (DSC) thermogram substantially as shown in FIG. 4B. Compound (I) edisylate exhibits a thermogravimetric analysis (TGA) thermogram substantially as shown in FIG. 4C. Compound (I) edisylate exhibits a dynamic vapor sorption (DVS) graph substantially as shown in FIG. 4D.

In some embodiments, Compound (I) edisylate has an XRPD pattern displaying at least two, at least three, at least four, or at least five of the degree 2θ-reflections with the greatest intensity as the XRPD pattern substantially as shown in FIG. 4A. It should be understood that relative intensities can vary depending on a number of factors, including sample preparation, mounting, and the instrument and analytical procedure and settings used to obtain the spectrum. As such, the peak assignments listed herein, including for Compound (I) edisylate, are intended to encompass variations of +/−0.2 degrees 2θ.

In certain embodiments, Compound (I) edisylate has an XRPD pattern comprising degree 2θ-reflections (+/−0.2 degrees 2θ) at 5.7, 16.6, and 24.2. In one embodiment, Compound (I) edisylate has an XRPD pattern comprising degree 2θ-reflections (+/−0.2 degrees 2θ) at 5.7, 11.1, 16.6, 22.2, and 24.2.

In certain embodiments, Compound (I) edisylate has a thermogravimetric analysis thermogram comprising a weight loss of about 4.0% from about 25° C. to about 100° C. In certain embodiments, Compound (I) edisylate has a differential scanning calorimetry curve comprising an endotherm at about 154° C. In certain embodiments, Compound (I) edisylate has a dynamic vapor sorption isotherm comprising a water uptake of about 22% from about 10% to about 90% RH at about 25° C. In some embodiments, Compound (I) edisylate has at least one, or both of the following properties:
  (a) an XRPD pattern substantially as shown in FIG. 4A;
  (b) a DSC thermogram substantially as shown in FIG. 4B.

Compound (I) Heminapadisylate

Figure 5A:
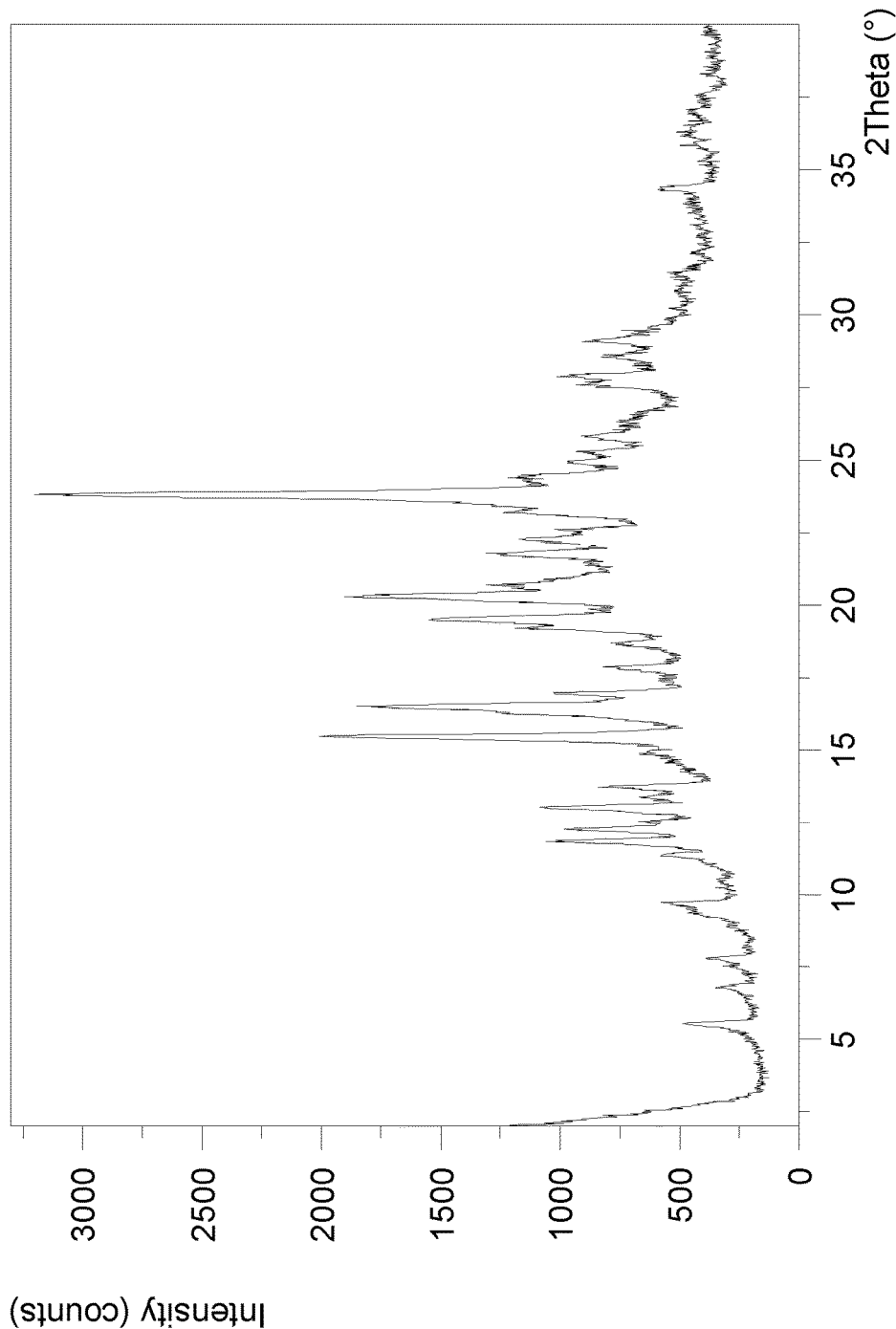
FIGS. 5A-5D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) heminapadisylate.
Figure 5B:
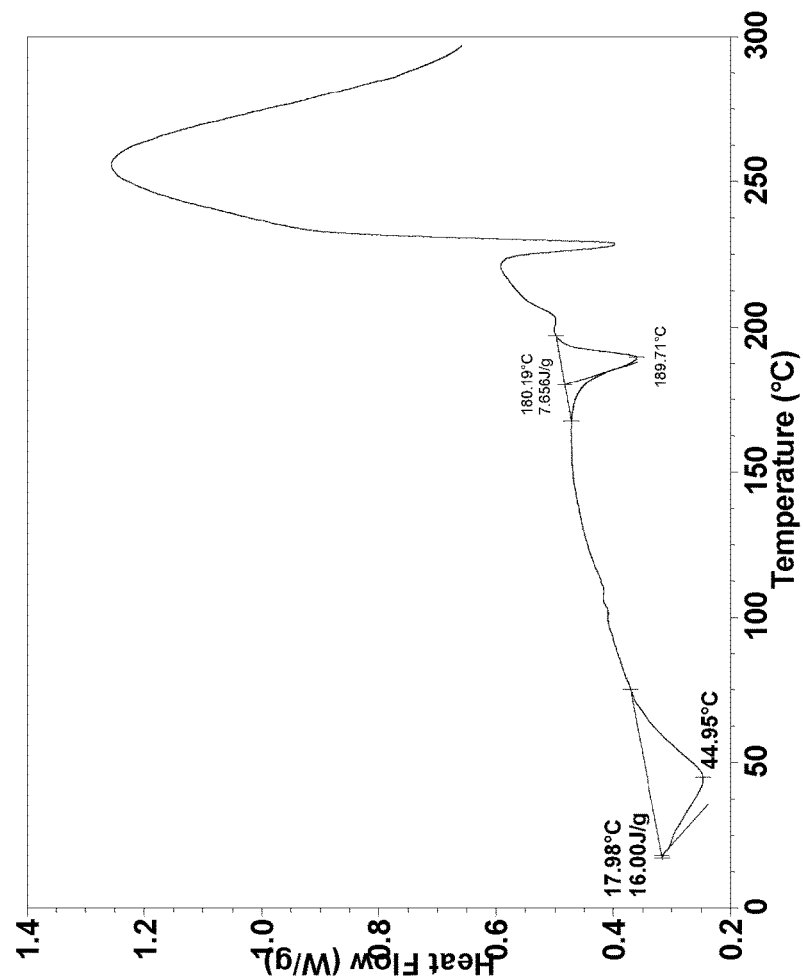
Figure 5C:
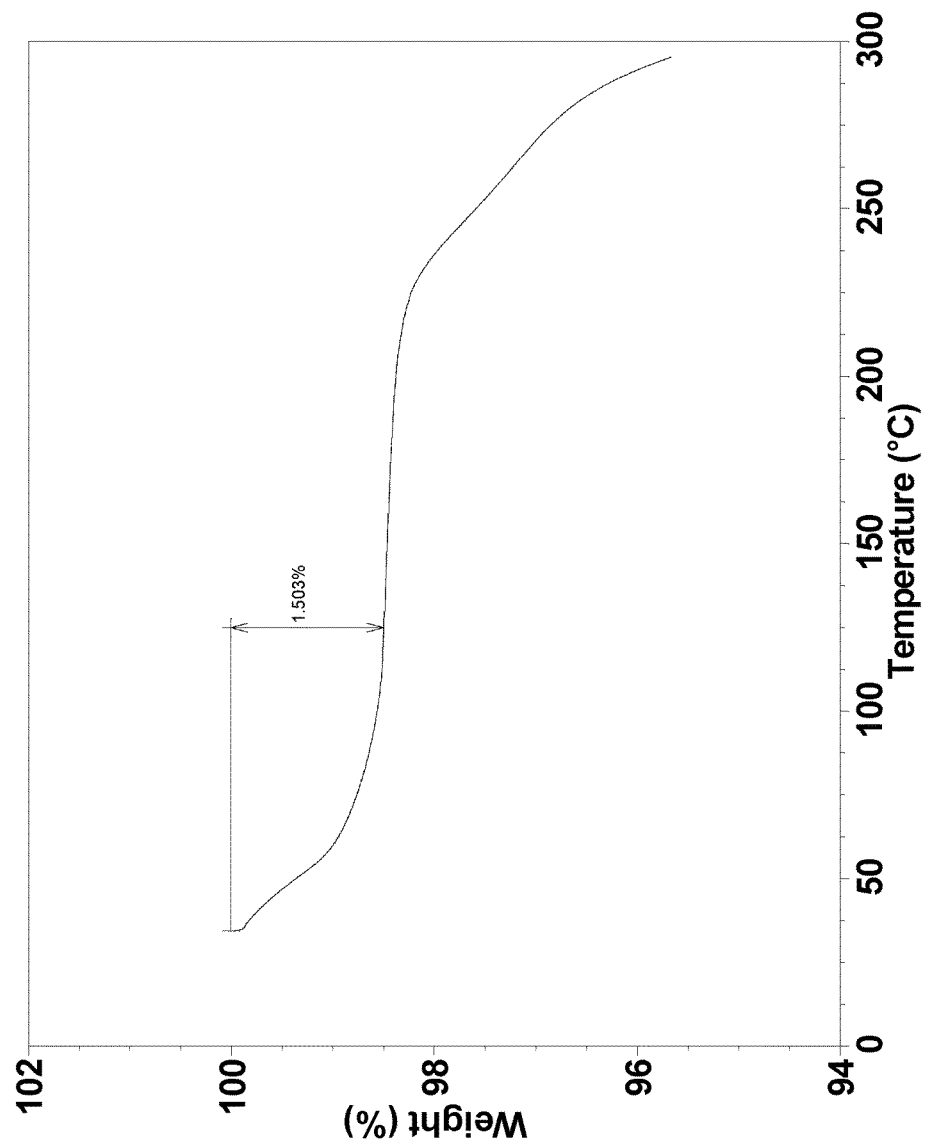
Figure 5D:
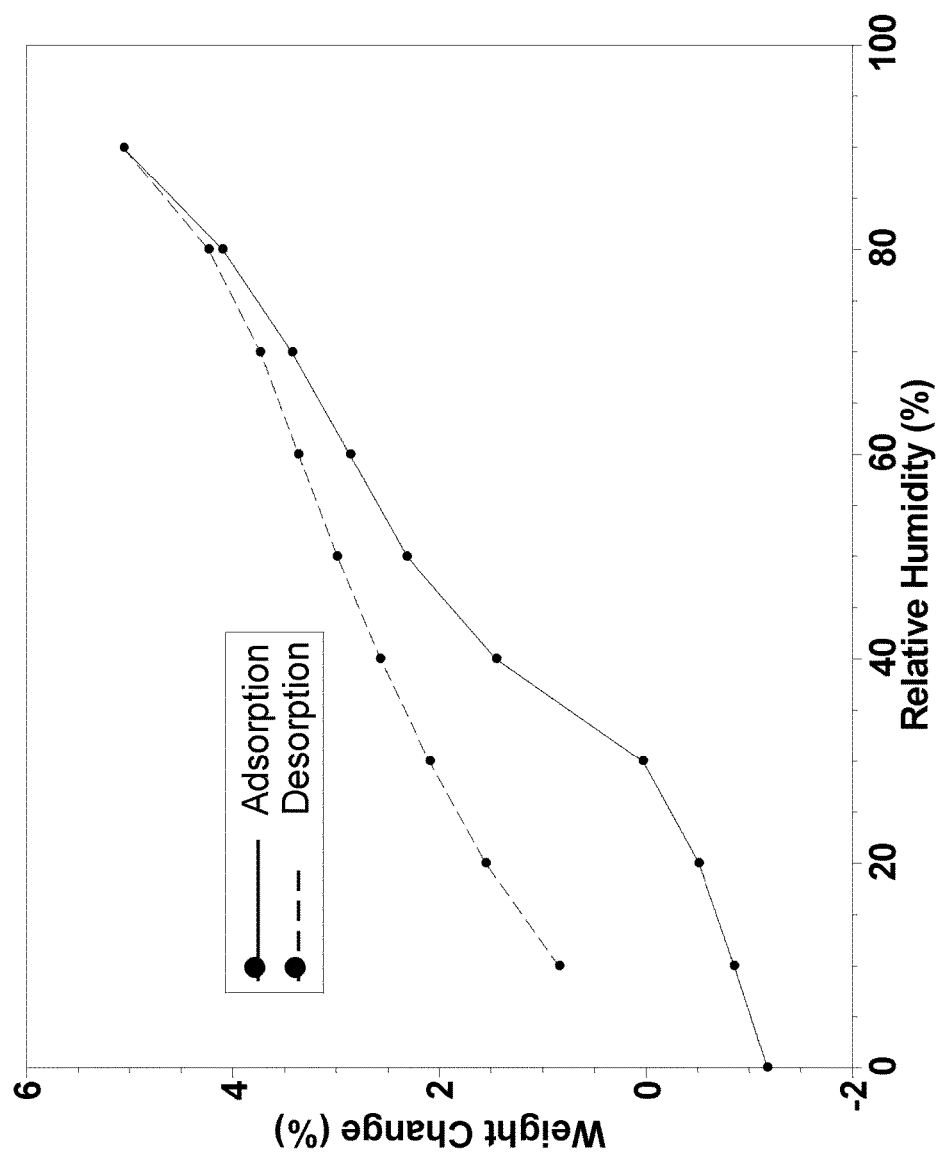

In one aspect, provided is Compound (I) heminapadisylate, wherein the crystalline form exhibits an XRPD pattern substantially as shown in FIG. 5A. Compound (I) heminapadisylate exhibits a differential scanning calorimetry (DSC) thermogram substantially as shown in FIG. 5B. Compound (I) heminapadisylate exhibits a thermogravimetric analysis (TGA) thermogram substantially as shown in FIG. 5C. Compound (I) heminapadisylate exhibits a dynamic vapor sorption (DVS) graph substantially as shown in FIG. 5D.

In some embodiments, Compound (I) heminapadisylate has an XRPD pattern displaying at least two, at least three, at least four, or at least five of the degree 2θ-reflections with the greatest intensity as the XRPD pattern substantially as shown in FIG. 5A. It should be understood that relative intensities can vary depending on a number of factors, including sample preparation, mounting, and the instrument and analytical procedure and settings used to obtain the spectrum. As such, the peak assignments listed herein, including for Compound (I) heminapadisylate, are intended to encompass variations of +/−0.2 degrees 2θ.

In certain embodiments, Compound (I) heminapadisylate has an XRPD pattern comprising degree 2θ-reflections (+/−0.2 degrees 2θ) at 15.5, 16.5, and 23.8. In one embodiment, Compound (I) heminapadisylate has an XRPD pattern comprising degree 2θ-reflections (+/−0.2 degrees 2θ) at 5.6, 15.5, 16.5, 20.3, and 23.8.

In certain embodiments, Compound (I) heminapadisylate has a thermogravimetric analysis thermogram comprising a weight loss of about 1.5% from about 25° C. to about 125° C. In certain embodiments, Compound (I) heminapadisylate has a differential scanning calorimetry curve comprising an endotherm at about 180° C. In certain embodiments, Compound (I) heminapadisylate has a dynamic vapor sorption isotherm comprising a water uptake of about 6.5% from about 10% to about 90% RH at about 25° C. In some embodiments, Compound (I) heminapadisylate has at least one, or both of the following properties:

(a) an XRPD pattern substantially as shown in FIG. 5A;
(b) a DSC thermogram substantially as shown in FIG. 5B.

Compound (I) Fumarate

Figure 6A:
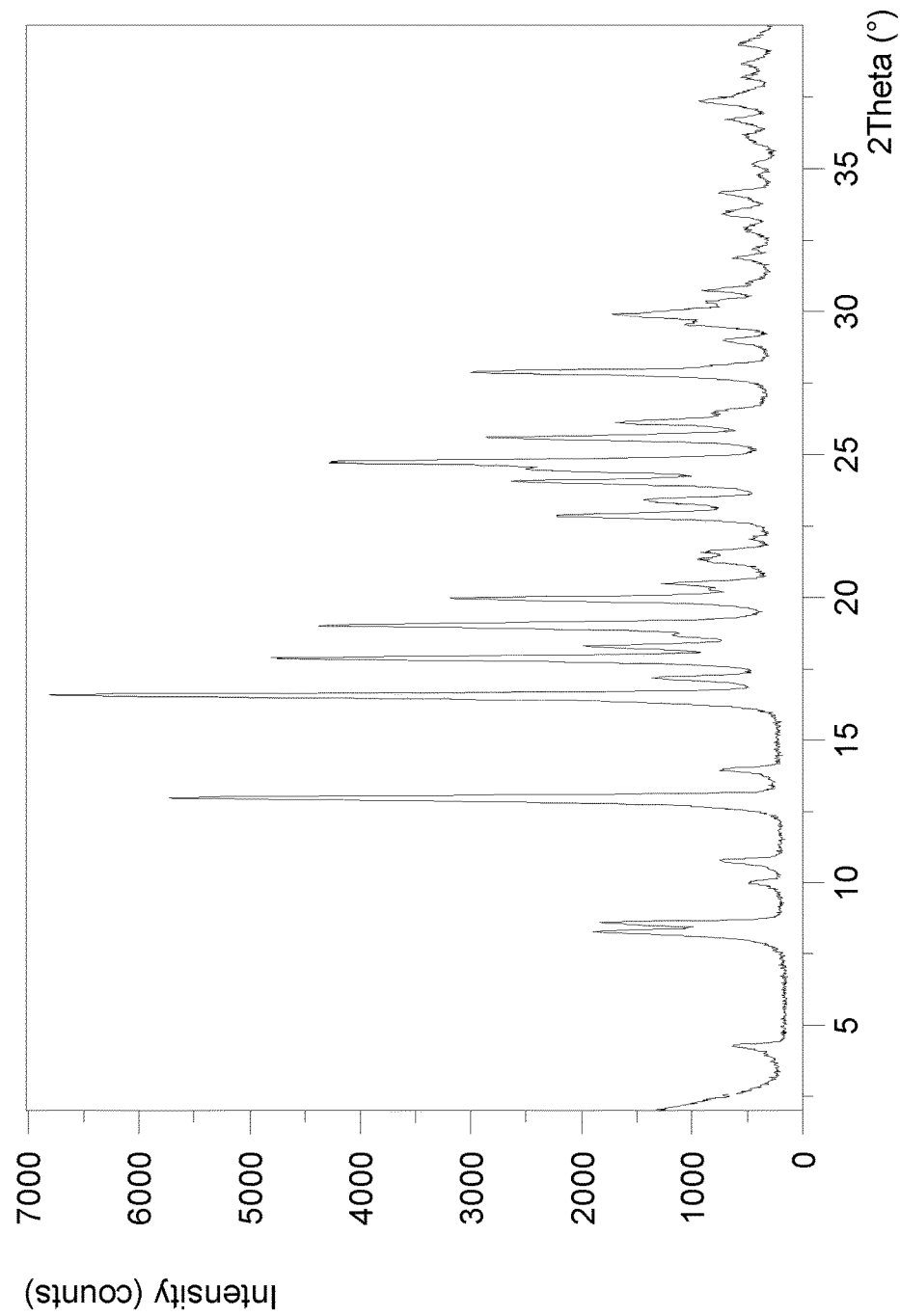
FIGS. 6A-6D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) fumarate.
Figure 6B:
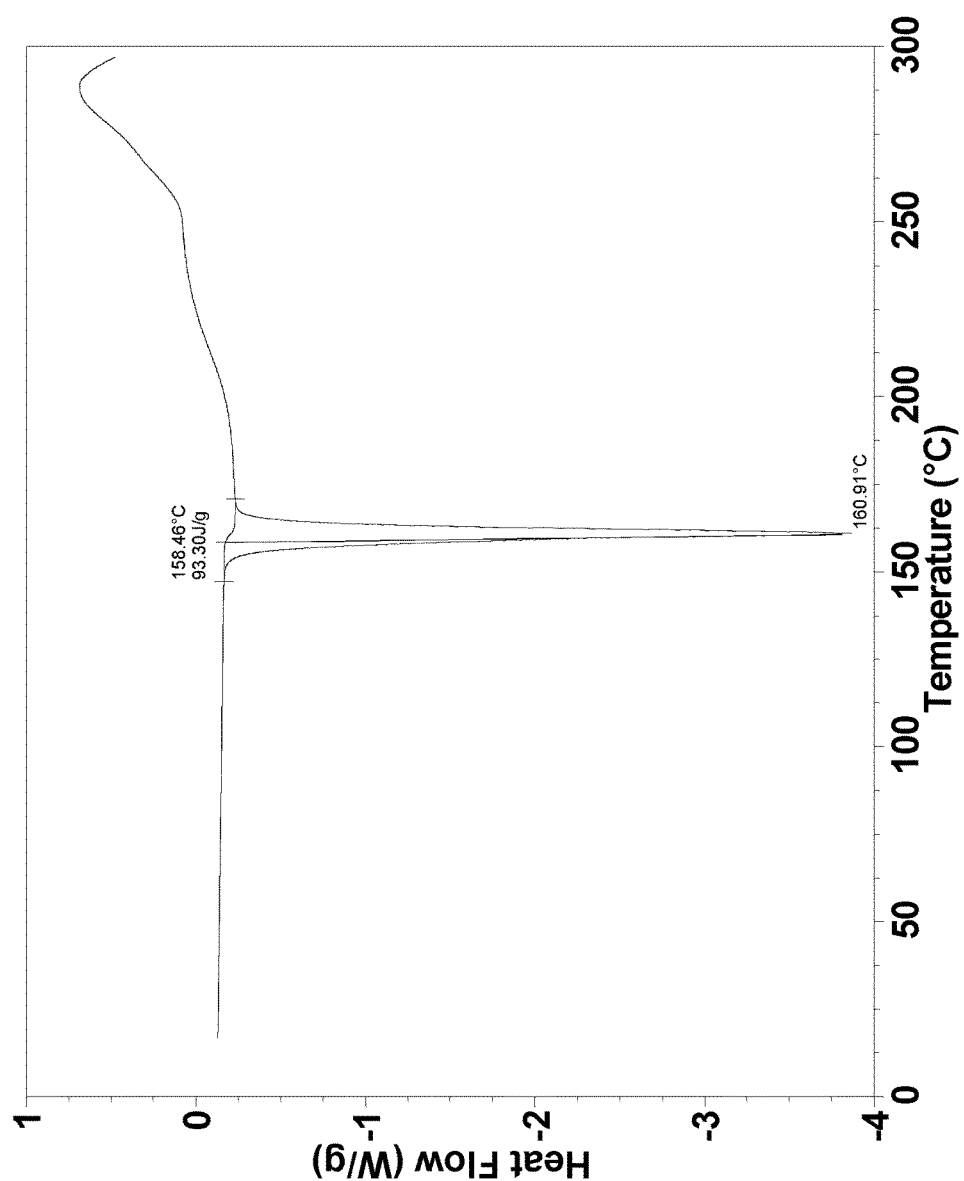
Figure 6C:
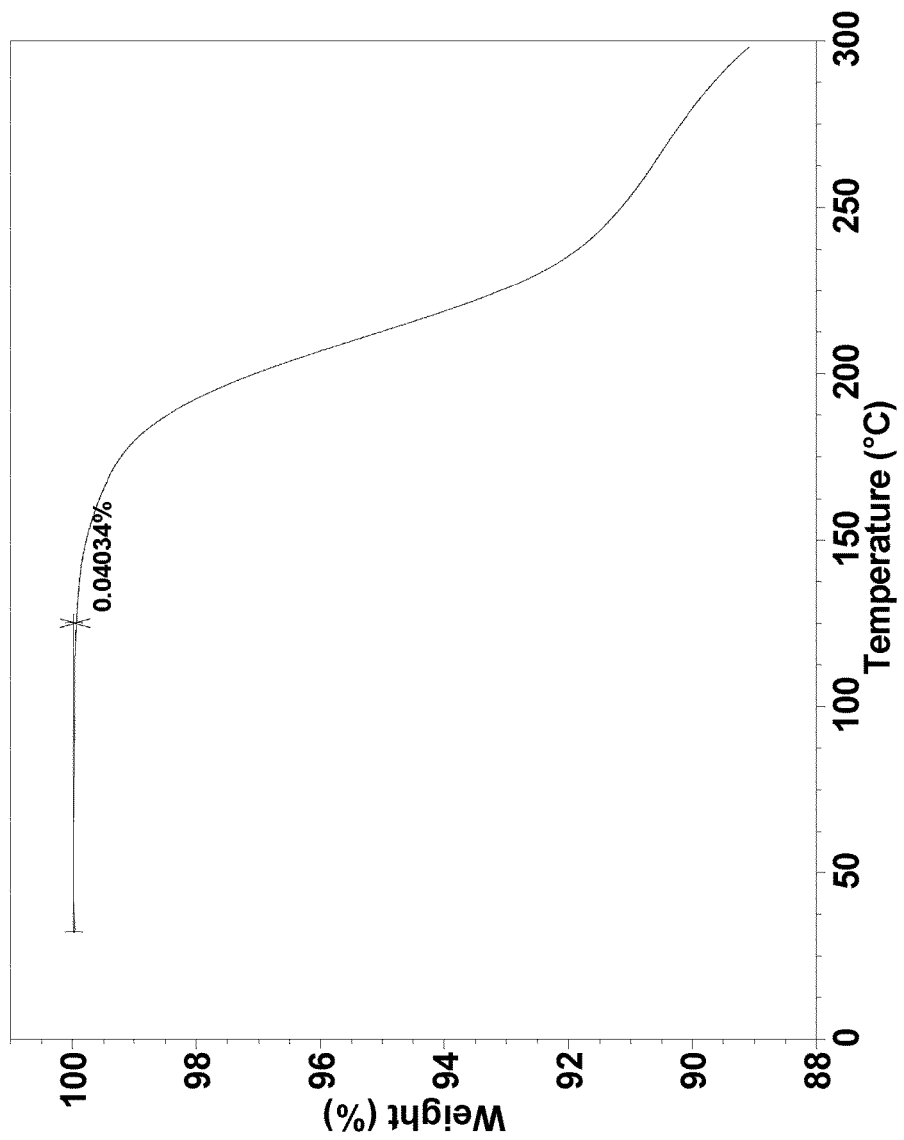
Figure 6D:
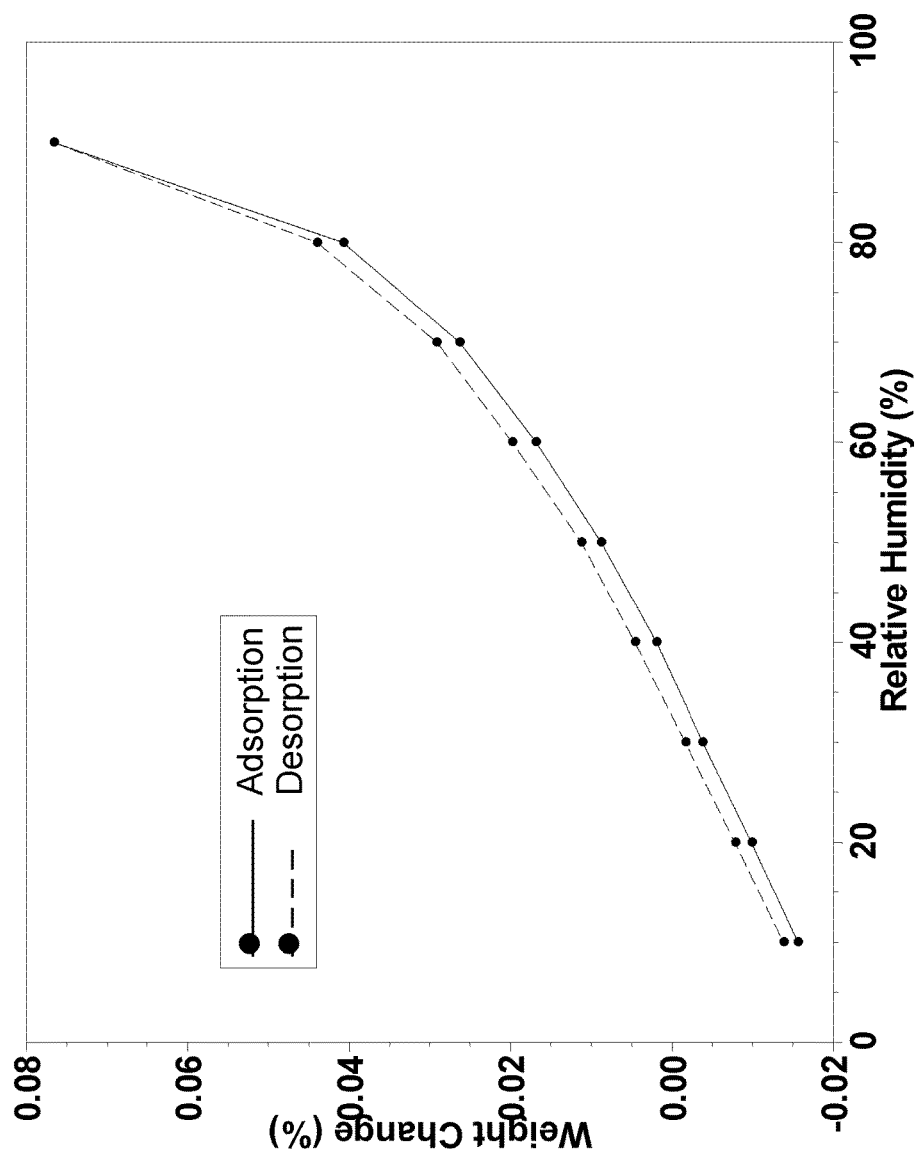

In one aspect, provided is Compound (I) fumarate, wherein the crystalline form exhibits an XRPD pattern substantially as shown in FIG. 6A. Compound (I) fumarate exhibits a differential scanning calorimetry (DSC) thermogram substantially as shown in FIG. 6B. Compound (I) fumarate exhibits a thermogravimetric analysis (TGA) thermogram substantially as shown in FIG. 6C. Compound (I) fumarate exhibits a dynamic vapor sorption (DVS) graph substantially as shown in FIG. 6D.

In some embodiments, Compound (I) fumarate has an XRPD pattern displaying at least two, at least three, at least four, or at least five of the degree 2θ-reflections with the greatest intensity as the XRPD pattern substantially as shown in FIG. 6A. It should be understood that relative intensities can vary depending on a number of factors, including sample preparation, mounting, and the instrument and analytical procedure and settings used to obtain the spectrum. As such, the peak assignments listed herein, including for Compound (I) fumarate, are intended to encompass variations of +/−0.2 degrees 2θ.

In certain embodiments, Compound (I) fumarate has an XRPD pattern comprising degree 2θ-reflections (+/−0.2 degrees 2θ) at 13.0, 16.6, and 19.9. In one embodiment, Compound (I) fumarate has an XRPD pattern comprising degree 2θ-reflections (+/−0.2 degrees 2θ) at 8.3, 13.0, 16.6, 19.0, and 19.9.

In certain embodiments, Compound (I) fumarate has a thermogravimetric analysis thermogram comprising a weight loss of about 0.04% from about 25° C. to about 100° C. In certain embodiments, Compound (I) fumarate has a differential scanning calorimetry curve comprising an endotherm at about 158° C. In certain embodiments, Compound (I) fumarate has a dynamic vapor sorption isotherm comprising a water uptake of about 0.1% from about 10% to about 90% RH at about 25° C. In some embodiments, Compound (I) fumarate has at least one, or both of the following properties:

(a) an XRPD pattern substantially as shown in FIG. 6A;
(b) a DSC thermogram substantially as shown in FIG. 6B.

Compound (I) Succinate

Figure 7A:
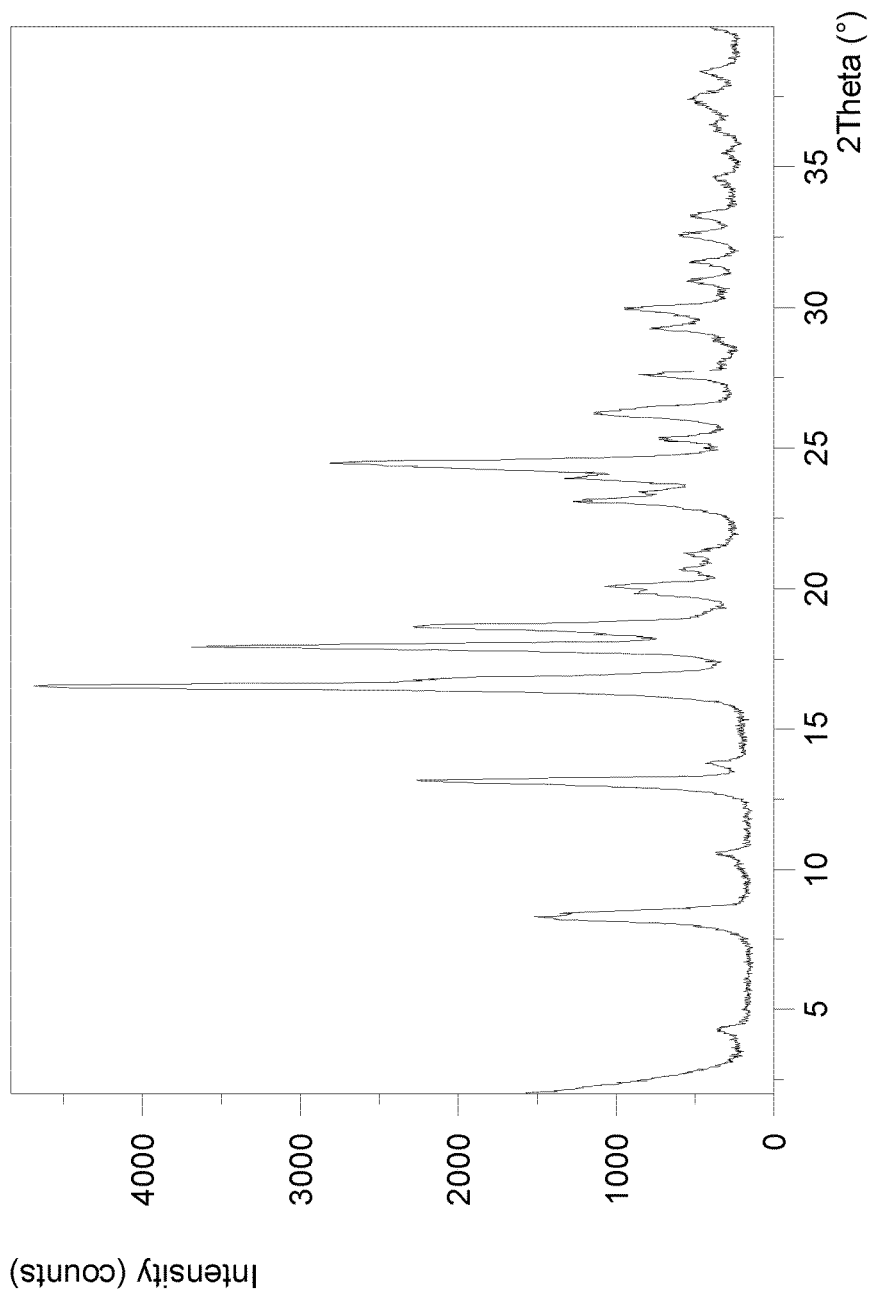
FIGS. 7A-7D show an X-ray powder diffraction pattern (XRPD) pattern, a differential scanning calorimetry (DSC) thermogram, a thermogravimetric analysis (TGA) thermogram, and a dynamic vapor sorption (DVS) graph, respectively, of Compound (I) succinate.
Figure 7B:
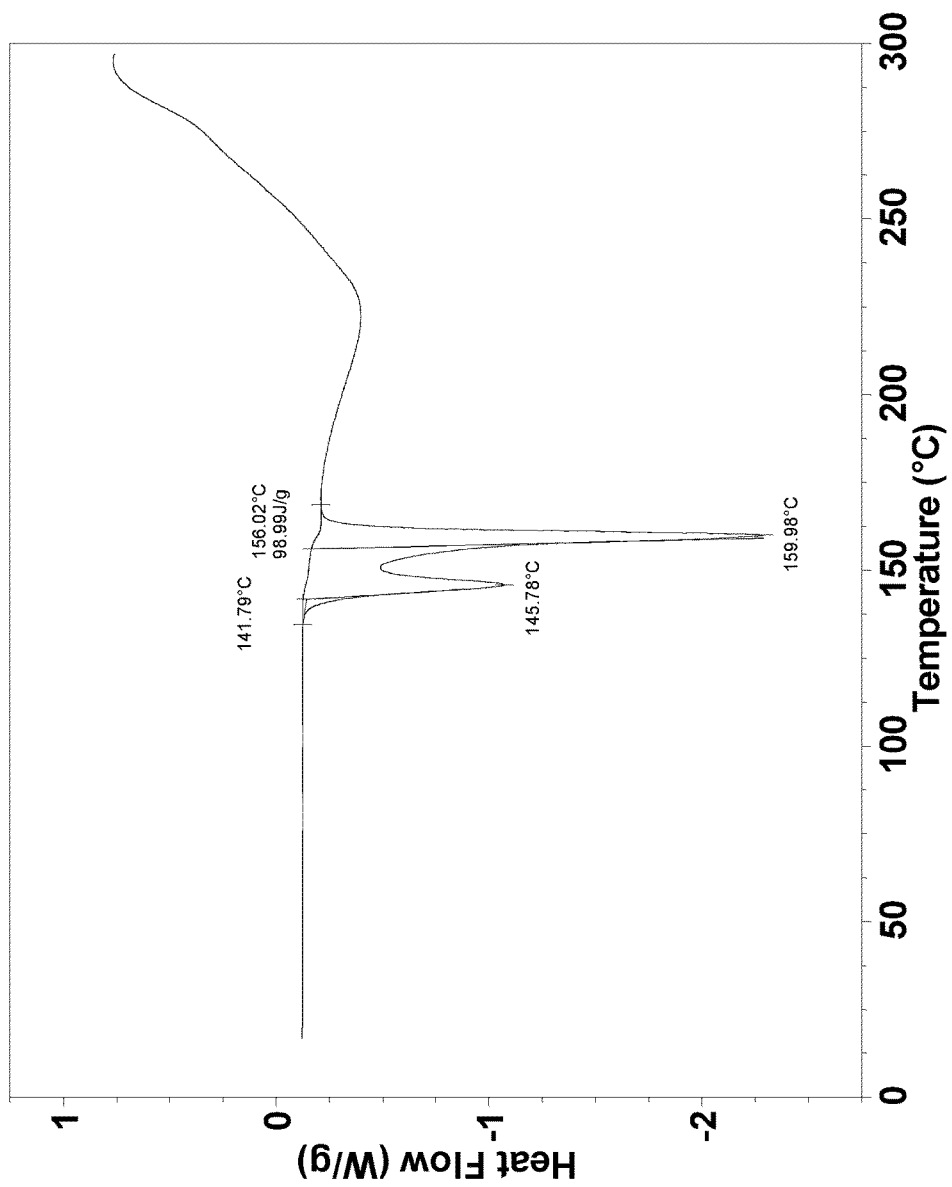
Figure 7C:
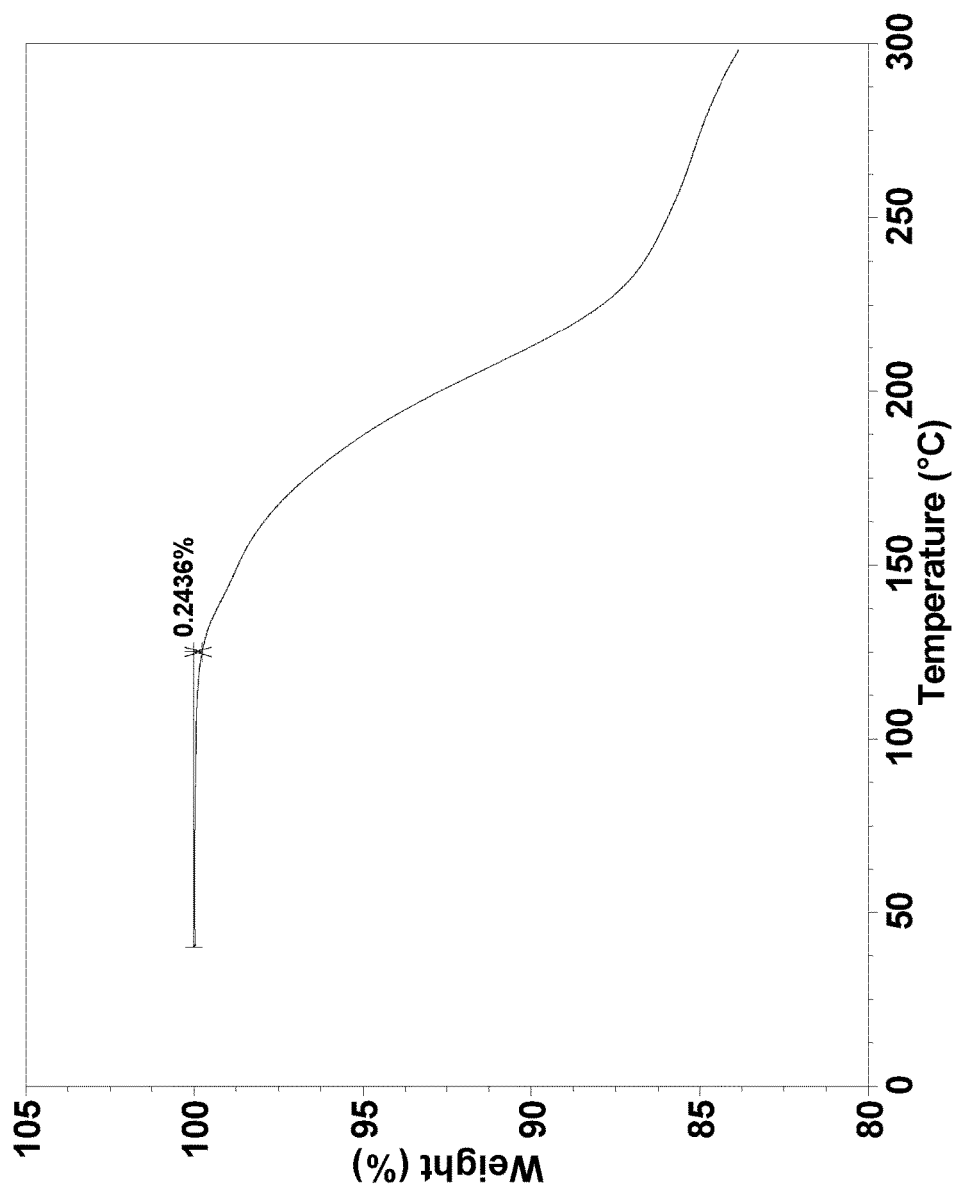
Figure 7D:
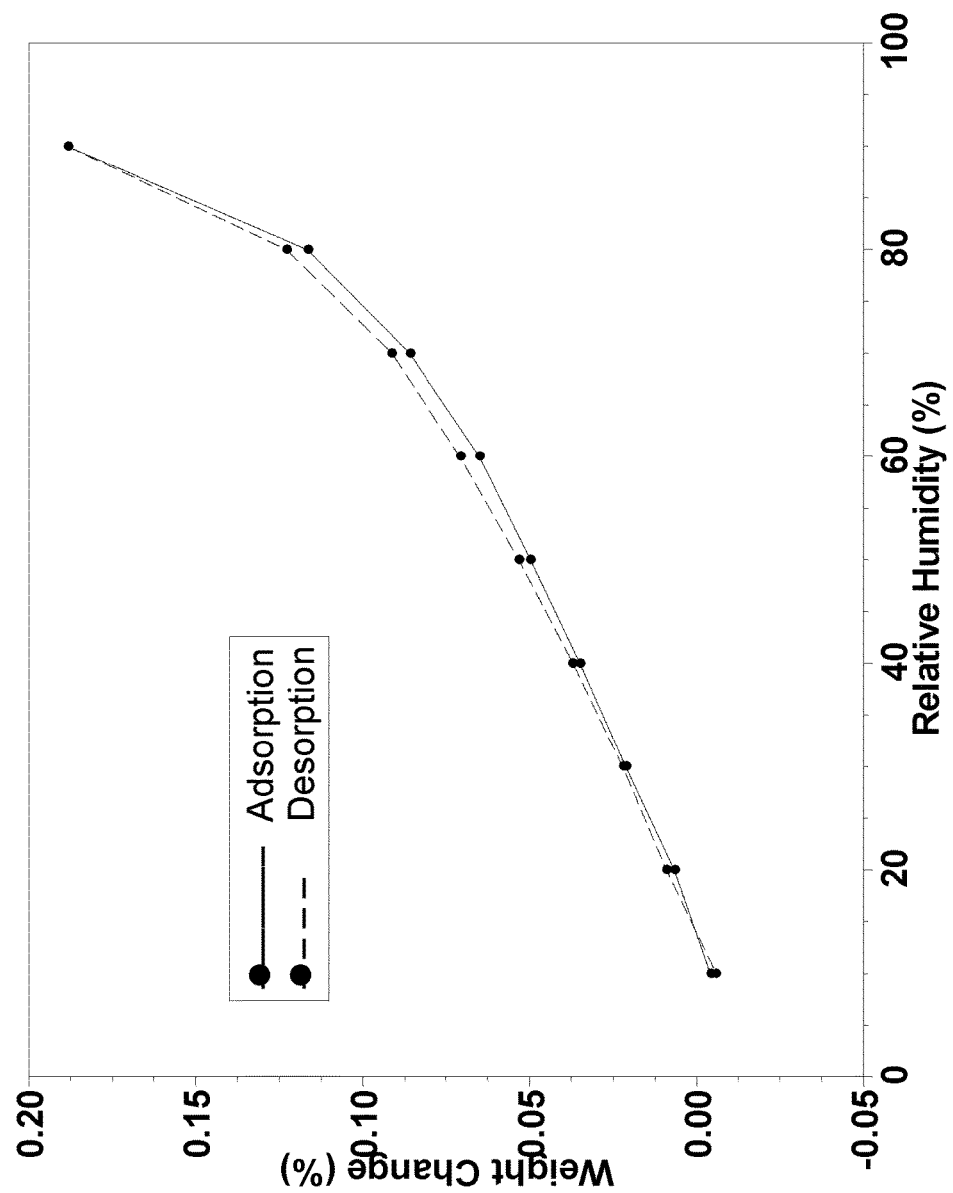

In one aspect, provided is Compound (I) succinate, wherein the crystalline form exhibits an XRPD pattern substantially as shown in FIG. 7A. Compound (I) succinate exhibits a differential scanning calorimetry (DSC) thermogram substantially as shown in FIG. 7B. Compound (I) succinate exhibits a thermogravimetric analysis (TGA) thermogram substantially as shown in FIG. 7C. Compound (I) succinate exhibits a dynamic vapor sorption (DVS) graph substantially as shown in FIG. 7D.

In some embodiments, Compound (I) succinate has an XRPD pattern displaying at least two, at least three, at least four, or at least five of the degree 2θ-reflections with the greatest intensity as the XRPD pattern substantially as shown in FIG. 7A. It should be understood that relative intensities can vary depending on a number of factors, including sample preparation, mounting, and the instrument and analytical procedure and settings used to obtain the spectrum. As such, the peak assignments listed herein, including for Compound (I) succinate, are intended to encompass variations of +/−0.2 degrees 2θ.

In certain embodiments, Compound (I) succinate has an XRPD pattern comprising degree 2θ-reflections (+/−0.2 degrees 2θ) at 13.2, 16.5, and 18.0. In one embodiment, Compound (I) succinate has an XRPD pattern comprising degree 2θ-reflections (+/−0.2 degrees 2θ) at 8.2, 13.2, 16.5, 18.0, and 18.6.

In certain embodiments, Compound (I) succinate has a thermogravimetric analysis thermogram comprising a weight loss of about 0.2% from about 25° C. to about 125° C. In certain embodiments, Compound (I) succinate has a differential scanning calorimetry curve comprising two endotherms at about 142° C. and about 160° C. In certain embodiments, Compound (I) succinate has a dynamic vapor sorption isotherm comprising a water uptake of about 0.2% from about 10% to about 90% RH at about 25° C. In some embodiments, Compound (I) succinate has at least one, or both of the following properties:

(a) an XRPD pattern substantially as shown in FIG. 7A;
(b) a DSC thermogram substantially as shown in FIG. 7B.

The compounds of the present invention have BTK inhibitory activity and as a result are useful as agents for preventing and/or treating BTK-related diseases, i.e., diseases in which B cells and/or mast cells participate, for example, allergic diseases, autoimmune diseases, inflammatory diseases, thromboembolic diseases, cancers, and graft-versus host diseases. The compounds of the present invention also exercise a selective inhibitory action on B cell activation and as a result are also effective as inhibitors of B cell activation.

Preparation

One method of synthesizing Compound (I) has been previously described in U.S. Pat. No. 8,557,803. This reference is hereby incorporated herein by reference in its entirety, and specifically with respect to the synthesis of Compound (I). The salt or co-crystal forms of Compound (I) described herein may be prepared from Compound (I). For example, in one aspect, provided are methods of producing a compositions comprising the salt or co-crystal forms of Compound (I) described herein, wherein the method comprises combining Compound (I) with a suitable acid and a suitable solvent or a mixture of suitable solvents to produce a composition comprising a salt or co-crystal form of Compound (I) described herein.

Acids suitable for salt or co-crystal formation may include, but are not limited to, for example, sulfuric acid, oxalic acid, ethane-1,2-disulfonic acid, naphthalene-1,5-disulfonic acid, fumaric acid and succinic acid. Solvents suitable for salt or co-crystal formation may include, but are not limited to, for example, methanol, ethanol, water, isopropyl acetate, ethyl acetate, methyl tert-butyl ether, n-heptane, acetonitrile, acetone, 2-methyltetrahydrofuran, tetrahydrofuran, methyl isobutyl ketone, methyl ethyl ketone, dichloromethane, 2-propanol, 1-propanol, 1-butanol, and any mixtures thereof. In another aspect, provided are also the salt or co-crystal forms of Compound (I) described herein produced according to any of the methods described herein.

In one embodiment, provided is a method of producing a composition comprising Compound (I) hemisulfate, wherein the method comprises (i) combining Compound (I) with sulfuric acid and a suitable solvent to obtain a mixture; (ii) heating the mixture obtained in step (i) to about 70° C.; (iii) cooling the mixture obtained in step (ii) to about 0° C.; and (iv) collecting the solid material obtained in step (iii) to obtain Compound (I) hemisulfate.

In another embodiment, provided is a method of producing a composition comprising Compound (I) oxalate, wherein the method comprises (i) combining Compound (I) with oxalic acid and a suitable solvent at about 21° C. to obtain a mixture; (ii) collecting the solid material obtained in step (i) to obtain Compound (I) oxalate.

In another embodiment, provided is a method of producing a composition comprising Compound (I) hemiedisylate, wherein the method comprises (i) combining Compound (I) with ethane-1,2-disulfonic acid dihydrate and a suitable solvent at about 21° C. to obtain a mixture; (ii) collecting the solid material obtained in step (i) to obtain Compound (I) hemiedisylate.

In another embodiment, provided is a method of producing a composition comprising Compound (I) edisylate, wherein the method comprises (i) combining Compound (I) with ethane-1,2-disulfonic acid dihydrate and a suitable solvent at about 21° C. to obtain a mixture; (ii) collecting the solid material obtained in step (i) to obtain Compound (I) edisylate.

In another embodiment, provided is a method of producing a composition comprising Compound (I) heminapadisylate, wherein the method comprises (i) combining Compound (I) with naphthalene-1,5-disulfonic acid and a suitable solvent to obtain a mixture; (ii) heating the mixture obtained in step (i) to about 50° C.; (iii) cooling the mixture obtained in step ii) to about 20° C.; and (iv) collecting the solid material obtained in step (iii) to obtain Compound (I) heminapadisylate.

In another embodiment, provided is a method of producing a composition comprising Compound (I) fumarate, wherein the method comprises (i) combining Compound (I) with fumaric acid and a suitable solvent; (ii) heating the mixture obtained in step (i) to about 50° C.; (iii) cooling the mixture obtained in step (ii) to about 20° C.; and (iv) collecting the solid material obtained in step (iii) to obtain Compound (I) fumarate.

In another embodiment, provided is a method of producing a composition comprising Compound (I) succinate, wherein the method comprises (i) combining Compound (I) with succinic acid and a suitable solvent; (ii) heating the mixture obtained in step (i) to about 50° C.; (iii) cooling the mixture obtained in step (ii) to about 20° C.; and (iv) collecting the solid material obtained in step (iii) to obtain Compound (I) succinate.

In some embodiments of the methods described above to produce the salt or co-crystal forms of Compound (I) described herein, the method further comprises isolating the salt or co-crystal from the resulting composition. Any suitable techniques or methods known in the art to isolate the salt or co-crystal forms from the compositions may be employed. For example, the solvent or mixture of solvents used in the methods described above may be removed by known methods, such as filtration and/or evaporation, to isolate the salt or co-crystal produced from the composition.

Compositions Uses of BTK Inhibitors

In some embodiments, the compositions described herein may comprise a substantially pure salt or co-crystal form of Compound (I) described herein or may be substantially free of other polymorphs and/or impurities. In some embodiments, the term "substantially pure" or "substantially free" with respect to a salt or co-crystal form of Compound (I) hemisulfate, oxalate, hemiedisylate, edisylate, heminapadisylate, fumarate, or succinate described herein means that the composition comprising the salt or co-crystal form of Compound (I) described herein contains less than 95%, less than 90%, less than 80%, less than 70%, less than 65%, less than 60%, less than 55%, less than 50%, less than 40%, less than 30%, less than 20%, less than 15%, less than 10%, less than 5%, or less than 1% by weight of other substances, including other polymorphic forms and/or impurities. In certain embodiments, "substantially pure" or "substantially free of" refers to a substance free of other substances, including other polymorphic forms and/or impurities. Impurities may, for example, include by-products or left over reagents from chemical reactions, contaminants, degradation products, other polymorphic forms, water, and solvents.

In some embodiments, the composition comprises a polymorphic form of a salt or co-crystal of Compound (I) described herein. In certain embodiments are provided compositions comprising a salt or co-crystal form of Compound (I) described herein, wherein the polymorphic form of the salt or co-crystal of Compound (I) within the composition is a substantially pure polymorphic form. In other embodiments of compositions comprising a polymorphic form of a salt or co-crystal of Compound (I) described herein, at least about 50%, at least about 60%, at least about 70%, at least about 80%, at least about 85%, at least about 90%, at least about 95%, at least about 96%, at least about 97%, at least about 98%, or at least about 99% of the salt or co-crystal of Compound (I) in the composition is in a polymorphic form of a salt or co-crystal of Compound (I) described herein.

In other embodiments of compositions comprising a polymorphic form of a salt or co-crystal of Compound (I) described herein, less than about 50%, less than about 40%, less than about 30%, less than about 20%, less than about 10%, less than about 5%, less than about 4%, less than about 3%, less than about 2% or less than about 1% of the salt or co-crystal of Compound (I) present in the composition are other polymorphic forms of salts or co-crystals of Compound (I) and/or impurities. In yet other embodiments of compositions comprising a salt or co-crystal form of Compound (I) described herein, impurities make up less than about 5%, less than about 4%, less than about 3%, less than about 2% or less than about 1% of the total mass relative to the mass of the salt or co-crystal form of Compound (I) described herein present. Impurities may, for example, include by-products from synthesizing the salt or co-crystal form of Compound (I) described herein, contaminants, degradation products, other polymorphic forms, water, and solvents.

In yet other embodiments, the composition comprising a salt or co-crystal form of Compound (I) described herein has less than about 5%, less than about 4%, less than about 3%, less than about 2%, or less than about 1% by weight of amorphous or non-crystalline forms of salts or co-crystals of Compound (I). In yet other embodiments, the composition comprising a salt or co-crystal form of Compound (I) described herein has less than about 5%, less than about 4%, less than about 3%, less than about 2%, or less than about 1% by weight of Compound (I) (i.e., in its free form).

The salt or co-crystal forms of Compound (I) described herein can be administered as the neat chemical, but it is typical, and preferable, to administer the compound in the form of a pharmaceutical composition or formulation. Accordingly, provided are pharmaceutical compositions comprising a salt or co-crystal form of Compound (I) described herein and one or more pharmaceutically acceptable carriers, excipients, or other ingredients (including inert solid diluents and fillers, diluents, including sterile aqueous solution and various organic solvents, permeation enhancers, solubilizers and adjuvants). The compositions can include a salt or co-crystal form of Compound (I) described herein either as the sole active agent or in combination with other agents, such as oligo- or polynucleotides, oligo- or polypeptides, drugs, or hormones mixed with one or more pharmaceutically acceptable carriers, excipients, or other ingredients. Carriers, excipients, and other ingredients can be deemed pharmaceutically acceptable insofar as they are compatible with other ingredients of the formulation and not deleterious to the recipient thereof.

Provided herein are pharmaceutical compositions comprising a salt or co-crystal form of Compound (I) described herein and a pharmaceutical acceptable carrier or excipient. Techniques for formulation and administration of pharmaceutical compositions can be found in Remington's Pharmaceutical Sciences, 18th Ed., Mack Publishing Co, Easton, Pa., 1990. The pharmaceutical compositions described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions can be formulated to contain suitable pharmaceutically acceptable carriers, and optionally can comprise excipients and auxiliaries that facilitate processing of the salt or co-crystal forms of Compound (I) described herein into preparations that can be used pharmaceutically. The mode of administration generally determines the nature of the carrier. For example, formulations for parenteral administration can include aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Alternatively, formulations for parenteral use can include dispersions or suspensions of a salt or co-crystal form of Compound (I) described herein prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT™ series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Liposomes containing the salt or co-crystal forms of Compound (I) described herein also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), Methods in Cell Biology, Vol. XIV, p. 33, Academic Press, New York (1976).

In some embodiments, the salt or co-crystal forms of Compound (I) described herein or compositions thereof disclosed herein are formulated for oral administration using pharmaceutically acceptable carriers, excipients or other ingredients well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or more excipients, which include, without limitation:

a) diluents, such as microcrystalline cellulose and sugars, including lactose, dextrose, sucrose, mannitol, or sorbitol;

b) binders, such as sodium starch glycolate, croscarmellose sodium, magnesium aluminum silicate, starch from corn, wheat, rice, potato, etc.;

c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as cross-linked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

For example, provided are tablets comprising a salt or co-crystal form of Compound (I) described herein and one or more pharmaceutically acceptable carriers or excipients. In one embodiment, the tablet is substantially free of amorphous or non-crystalline forms of Compound (I). In another embodiment the tablet is substantially free of free (base) Compound (I).

Gelatin capsules include push-fit capsules made of gelatin, as well as soft, sealed capsules made of gelatin and a coating such as glycerol or sorbitol. Push-fit capsules can contain the active ingredient mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers. Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, or ampoule). The salt or co-crystal forms of Compound (I) described herein are effective over a wide dosage range and are generally administered in a pharmaceutically effective amount. It will be understood, however, that the amount of the salt or co-crystal form of Compound (I) described herein actually administered will be determined by a physician, in the light of the relevant circumstances, including the condition to be treated, the chosen route of administration, the age, weight, and response of the subject receiving such treatment, the severity of the subject's symptoms, and the like.

The tablets or pills described herein may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. The two elements can be separated by an enteric layer that serves to resist disintegration in the stomach and permit the inner element to pass intact into the duodenum or to be delayed in release. A variety of materials can be used for such enteric layers or coatings, such materials including a number of polymorphic acids and mixtures of polymorphic acids with such materials as shellac, cetyl alcohol, and cellulose acetate.

For example, provided are unit dosages comprising a salt or co-crystal form of Compound (I) described herein. Exemplary unit dosage levels of the salt or co-crystal forms of Compound (I) described herein for a human subject may, in certain variations, be between about 0.01 mg to about 1000 mg, or between about 1 mg to about 200 mg, or between about 10 mg to about 200 mg, or between about 20 mg to about 160 mg, or between about 10 mg to about 100 mg, or between about 50 mg to about 175 mg, or between about 20 mg to about 150 mg, or between about 75 mg to about 100 mg, or between about 100 mg to about 200 mg. Individual doses of the salt or co-crystal forms of Compound (I) described herein that may be administered to a human in need thereof include individual doses of 1 mg, 5 mg, 10 mg, 20 mg, 30 mg, 40 mg, 50 mg, 60 mg, 70 mg, 75 mg, 80 mg, 90 mg, 100 mg, 110 mg, 120 mg, 130 mg, 140 mg, 150 mg, 160 mg, 170 mg, 175 mg, and 200 mg. The doses of the salt or co-crystal forms of Compound (I) described herein may be administered as determined by a medical professional and may be administered once daily or may be delivered twice daily, three times daily, or four times daily. In one embodiment, the salt or co-crystal form of Compound (I) described herein is administered orally, once a day, to a subject in need thereof at a dose of 20 mg, 40 mg, 80 mg, or 150 mg. In some embodiments, the salt or co-crystal form of Compound (I) described herein is administered orally, twice a day, to a subject at a dose of 20 mg, 40 mg, or 75 mg. In additional embodiment, the therapeutically effective amount of the BTK inhibitor described herein is a dose of from about 1 mg to about 200 mg. In another embodiment, the BTK inhibitor described herein is administered at a dose of from about 10 mg to about 200 mg. In another embodiment, the BTK in a human is administered at a dose of from about 20 mg to about 160 mg. In other embodiment, the BTK inhibitor is administered to a human at a dose of: a) from about 10 mg to about 100 mg, b) from about 50 mg to about 175 mg, c) from about 20 mg to about 150 mg, d) from about 75 mg to about 100 mg, and e) from about 100 mg to about 200 mg. Individual doses of the BTK inhibitor that may be administered to a human in need thereof include individual doses of 1 mg, 5 mg, 10 mg, 20 mg, 30 mg, 40 mg, 50 mg, 60 mg, 70 mg, 75 mg, 80 mg, 901 mg, 100 mg, 110 mg, 120 mg, 130 mg, 140 mg, 150 mg, 160 mg, 170 mg, 175 mg, and 200 mg. The doses of the BTK inhibitor may be administered as determined by a medical professional and may be administered once daily or may be delivered twice daily, three times daily, or four times daily. In one embodiment, the method of the present application comprises administering a BTK inhibitor of Formulae (I)-(III) or a composition thereof at a dose of 10 mg, 20 mg, 40 mg, 80 mg, 150 mg, or 200 mg daily. In other embodiment, the method of the present application comprises administering a BTK inhibitor of Formulae (I)-(III) or a composition thereof at a dose of 20 mg, 40 mg, 80 mg, or 150 mg daily.

Modes of Administration and Dosages

Pharmaceutical compositions including a salt or co-crystal form of Compound (I) described herein can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral, buccal, sublingual, and rectal administration. Transepithelial administration modalities include, for example, transmucosal administration and transdermal administration. Transmucosal administration includes, for example, enteral administration as well as nasal, inhalation, and deep lung administration; vaginal administration; and buccal and sublingual administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT™.

Pharmacokinetic and pharmacodynamic information about a salt or co-crystal form of Compound (I) described herein and a formulation of a salt or co-crystal form of Compound (I) described herein can be collected through preclinical in vitro and in vivo studies, later confirmed in humans during the course of clinical trials. Thus, for a salt or co-crystal form of Compound (I) described herein used in the methods described herein, a therapeutically effective dose can be estimated initially from biochemical and/or cell-based assays. Then, dosage can be formulated in animal models to achieve a desirable circulating concentration range that modulates BTK expression or activity. As human studies are conducted further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the ED.sub.50 with little or no toxicity.

It should be understood that any effective administration regimen regulating the timing and sequence of doses can be used. A salt or co-crystal form of Compound (I) described herein and pharmaceutical compositions thereof may include those wherein the active ingredient is administered in an effective amount to achieve its intended purpose. In some embodiments, a "therapeutically effective amount" means an amount sufficient to modulate BTK expression or activity, including, and thereby treat a subject (e.g., a human) suffering an indication, or to alleviate the existing symptoms of the indication.

Exemplary dosage levels for a human subject are of the order of from about 0.001 milligram of active agent per kilogram body weight (mg/kg) to about 1000 mg/kg. Typically, dosage units of the active agent comprise from about 0.01 mg to about 1000 mg, preferably from about 0.1 mg to about 100 mg, depending upon the indication, route of administration, and severity of the condition, for example. Depending on the route of administration, a suitable dose can be calculated according to body weight, body surface area, or organ size. The final dosage regimen is determined by the attending physician in view of good medical practice, considering various factors that modify the action of drugs, e.g., the specific activity of the compound, the identity and severity of the disease state, the responsiveness of the subject, the age, condition, body weight, sex, and diet of the subject, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing depends on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks.

Uses of BTK Inhibitors

Provided are uses of the salt or co-crystal forms of Compound (I) described herein; and or compositions thereof described herein to selectively or specifically inhibit BTK activity therapeutically or prophylactically. The method comprises administering a salt or co-crystal form of Compound (I) described herein or compositions thereof to a subject (e.g., a human) in need thereof in an amount sufficient to inhibit BTK activity. The method can be employed to treat humans or animals suffering from, or subject to, a condition whose symptoms or pathology is mediated by BTK expression or activity.

"Treatment" or "treating" is an approach for obtaining beneficial or desired results including clinical results. Beneficial or desired clinical results may include one or more of the following:

(i) decreasing one more symptoms resulting from the disease;

(ii) diminishing the extent of the disease and/or stabilizing the disease (e.g., delaying the worsening of the disease);

(iii) delaying the spread (e.g., metastasis) of the disease;

(iv) delaying or slowing the recurrence of the disease and/or the progression of the disease;

(v) ameliorating the disease state and/or providing a remission (whether partial or total) of the disease and/or decreasing the dose of one or more other medications required to treat the disease;

(vi) increasing the quality of life, and/or (vii) prolonging survival.

In some embodiments, "disorder" is intended to encompass medical disorders, diseases, conditions, syndromes, and the like, without limitation. The methods disclosed in the application embrace various modes of treating an animal subject, preferably a mammal, more preferably a primate, and still more preferably a human. Among the mammalian animals that can be treated are, for example, humans; companion animals (pets), including dogs and cats; farm animals, including cattle, horses, sheep, pigs, and goats; laboratory animals, including rats, mice, rabbits, guinea pigs, and nonhuman primates; and zoo specimens. Among the non-mammalian animals that can be treated include, for example, birds, fish, reptiles, and amphibians.

In one aspect, the salt or co-crystal forms of Compound (I) described herein and compositions thereof described herein can be employed in methods of inhibiting the growth or proliferation of cancer cells of hematopoietic origin, such as cancer cells. In some embodiments, the cancer cells are of lymphoid origin, and in specific embodiments, the cancer cells are related to or derived from B lymphocytes or B lymphocyte progenitors. In another aspect, the salt or co-crystal forms of Compound (I) described herein and compositions thereof described herein can be employed in methods of treating a human with a cancer.

Cancers amenable to treatment using the method disclosed in the application include, for example, non-Hodgkin's lymphomas, among which B-cell non-Hodgkin's lymphomas are particularly suitable, for example, Burkitt's lymphoma, AIDS-related lymphoma, marginal zone B-cell lymphoma (nodal marginal zone B-cell lymphoma, extranodal marginal zone B-cell lymphoma, and splenic marginal zone B-cell lymphoma), diffuse large B-cell lymphoma, primary effusion lymphoma, lymphomatoid granulomatosis, follicular lymphoma, B-cell chronic lymphocytic leukemia, B-cell prolymphocytic leukemia, lymphoplasmacytic leukemia/Waldenstrom's macroglobulinemia, plasmacytoma, mantle cell lymphoma, mediastinal large B-cell lymphoma, intravascular large B-cell lymphoma, and hairy cell leukemia. In addition to non-Hodgkin's lymphoma, the cancers in the present invention include pancreatic endocrine tumors, for example, insulinoma, gastrinoma, glucagonoma, somatostatinoma, VIPoma, PPoma, and GRFoma. Other cancer cells, of hematopoietic origin or otherwise, that express BTK also can be treated by administration of the salt or co-crystal forms of Compound (I) described herein and compositions thereof described herein.

In another aspect, the salt or co-crystal forms of Compound (I) described herein and compositions thereof described herein can be employed in methods of treating an autoimmune disease. In particular embodiments, the autoimmune disease is inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Basedow's disease, Sjôgren's syndrome, multiple sclerosis, Guillain-Barrë syndrome, acute disseminated encephalomyelitis, Addison's disease, opsoclonus-myoclonus syndrome, ankylosing spondylitis, anti-phospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu's arteritis, temporal arteritis, warm autoimmune hemolytic anemia, Wegener's granuloma, psoriasis, alopecia universalis, Behget's disease, chronic fatigue syndrome, dysautonomia, endometriosis, interstitial cystitis, myotonia, vulvodynia, and systemic lupus erythematosus.

In yet another aspect, provided are methods of treating a human having a BTK-mediated disorder by administering a salt or co-crystal form of Compound (I) described herein to the human. Provided are also methods of modulating BTK an individual by administering a salt or co-crystal form of Compound (I) described herein. In one variation, the human has cancer, such as leukemia or lymphoma. In another variation, the human has an autoimmune disease, such as asthma, rheumatoid arthritis, multiple sclerosis, or lupus.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein, an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof. These therapeutic agents may be in the forms of compounds, antibodies, polypeptides, or polynucleotides. In one embodiment, the application provides a product comprising a compound described herein and an additional therapeutic agent as a combined preparation for simultaneous, separate, or sequential use in therapy, e.g. a method of treating a disease, disorder, or condition that is mediated by BTK.

The one or more therapeutic agents include, but are not limited to, an inhibitor, agonist, antagonist, ligand, modulator, stimulator, blocker, activator or suppressor of a gene, ligand, receptor, protein, factor such as: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C-C motif) receptor (such as CCR2, CCR4, CCR5), chemokine (C-X-C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COPS signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIFSA) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase, Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyl-transferase, Galectin-3, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releaseing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha, Imprinted Maternally Expressed Transcript (H19) gene, mitogen-activated protein kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KISS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyl-transferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

One aspect provides the methods of treating a human having a BTK-mediated disorder by administering a BTK inhibitor of Formulae (I)-(III) to the human in combination with one or more other therapeutic agents selecting from the group of an apoptosis signal-regulating kinase (ASK) inhibitor, a discoidin domain receptor (DDR) inhibitor, a histone deacetylase (HDAC) inhibitor, a Janus kinase (JAK) inhibitor, a lysyl oxidase-like protein 2 (LOXL2) inhibitor, a matrix metalloprotease 9 (MMP9) inhibitor, a phosphatidylinositol 3-kinase (PI3K) inhibitor, a spleen tyrosine kinase (SYK) inhibitor, a BET-bromodomain 4 (BRD4) inhibitor, a checkpoint inhibitor, a B-cell chronic lymphocytic leukemia (CLL)/lymphoma 2 (BCL-2) inhibitor and a CD20 inhibitor. In any of the foregoing methods, the BTK inhibitors of Formulae (I)-(III) may be administered to the individual as a unit dosage, for example in the form of a tablet, as described herein. Also, in any of the foregoing methods, the BTK inhibitors of Formulae (I)-(III) and one or more therapeutic agents may be administered simultaneously or sequentially.

Examples of one or more therapeutic agents include, but are not limited to, ASK inhibitors include ASK1 inhibitors as those described in WO 2011/008709 and WO 2013/112741; CD47 inhibitors such as anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621; CDK inhibitors such as abemaciclib, alvocidib (HMR-1275, flavopiridol), AT-7519, FLX-925, LEE001, palbociclib, ribociclib, rigosertib, selinexor, UCN-01, and TG-02; DDR inhibitors such as those disclosed in PCT Pub. Nos. WO 2014/047624, WO 2013/027802, and WO 2013/034933, U.S. Pub. Patent App. No. 2011/0287011 and 2009/0142345; HDAC inhibitors such as abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat; IDO1 inhibitors such as BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST; JAK inhibitors such as AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019; LOXL inhibitors such as the antibodies described in WO 2009/017833, WO 2009/035791, and WO 2011/097513; MMP9 inhibitors such as marimastat (BB-2516), cipemastat (Ro 32-3555) and those described in PCT Pub. No. WO 2012/027721; MEK inhibitors such as antroquinonol, binimetinib, cobimetinib (GDC-0973, XL-518), MT-144, selumetinib (AZD6244), sorafenib, trametinib (GSK1120212), uprosertib+trametinib; PI3K inhibitors such as ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in PCT Pub. Nos. WO 2005/113556, WO 2013/052699, WO 2013/116562, WO 2014/100765, WO 2014/100767, and WO 2014/201409; SYK inhibitors such as 6-(1H-indazol-6-yl)-N-(4-morpholinophenyl)imidazo [1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 and U.S. Pub. Patent App. No. 2015/0175616; TLR8 inhibitors such as E-6887, IMO-4200, IMO-8400, IMO-9200, MCT-465, MEDI-9197, motolimod, resiquimod, VTX-1463, and VTX-763; TLR9 inhibitors such as IMO-2055, IMO-2125, lefitolimod, litenimod, MGN-1601, and PUL-042; TKIs inhibitors such as afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000.

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above. Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors. Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®). Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®). Examples of anti-androgens include apalutamide, abiraterone, enzalutamide, flutamide, galeterone, nilutamide, bicalutamide, leuprolide, goserelin, ODM-201, APC-100, ODM-204. Examples of progesterone receptor antagonist include onapristone.

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456; 5,059,714; 5,120,764; 5,182,297; and 5,252,608 relating to 2-(1-naphthyloxymemyl)-3-fluoroallylamine, and U.S. Pub. Patent App. No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone. Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio) butane sulphurate, 2-acetamidoethyl-2-acetamidoethanethiol sulphanate, and sodium-4-mercaptobutanesulphinate trihydrate.

The immunotherapeutic agents include and are not limited to therapeutic antibodies suitable for treating patients. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, 3F8, and the like. Rituximab can be used for treating indolent B-cell cancers, including marginal-zone lymphoma, WM, CLL and small lymphocytic lymphoma. A combination of Rituximab and chemotherapy agents is especially effective. The exemplified therapeutic antibodies may be further labeled or combined with a radioisotope particle such as indium-111, yttrium-90 (90Y-clivatuzumab), or iodine-131. It is understood that, the agents, molecules, compounds, or antibodies described above may have additional mode of mechanism and would not be limited to the mode described above; for example, a chemotherapy agent may be an anti-fibrotic agent.

Provided are uses of the salt or co-crystal forms of Compound (I) described herein in the manufacture of a drug product. The salt or co-crystal forms of Compound (I) described herein may serve as intermediates in the manufacturing process to produce the drug product.

Articles of Manufacture and Kits

Compositions comprising a salt or co-crystal form of Compound (I) described herein and formulated in one or more pharmaceutically acceptable carriers, excipients or other ingredients can be prepared, placed in an appropriate container, and labeled for treatment of an indicated condition. Accordingly, there also is contemplated articles of manufacture, such as containers comprising dosage forms of a salt or co-crystal form of Compound (I) described herein and labels containing instructions for use of the compound.

In some embodiments, the articles of manufacture are containers comprising dosage forms of a salt or co-crystal form of Compound (I) described herein and one or more pharmaceutically acceptable carriers, excipients or other ingredients. In one embodiment of the articles of manufacture described herein, the dosage form is a tablet.

Kits also are contemplated. For example, a kit can comprise a dosage form of a pharmaceutical composition and a package insert containing instructions for use of the composition in treatment of a medical condition. The instructions for use in the kit may be for treating a BTK-mediated disorder, including, for example, an autoimmune disease or a cancer. In certain embodiments, conditions indicated on the label can include, for example, treatment of an autoimmune disease or a cancer.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

The salt and co-crystal forms of 6-amino-9-[(3R)-1-(2-butynoyl)-3-pyrrolidinyl]-7-(4-phenoxyphenyl)-7,9-dihydro-8H-purin-8-one were characterized by various analytical techniques, including X-ray powder diffraction pattern (XRPD), differential scanning calorimetry (DSC), and thermogravimetric analysis (TGA) using the procedures described below.

X-Ray Powder Diffraction (XRPD):

XRPD patterns were collected on a PANanalytical XPERT-PRO diffractometer at ambient conditions under the following experimental settings: 45 KV, 40 mA, Kα1=1.5406 Å, scan range 2 to 40°, step size 0.0084 or 0.0167°, measurement time: 5 min.

Differential Scanning Calorimetry (DSC):

DSC thermograms were collected on a TA Instruments Q2000 system equipped with a 50 position auto-sampler. The calibration for energy and temperature was carried out using certified indium. Typically 1-5 mg of each sample, in a pin-holed aluminium pan, was heated at 10° C./min from 25° C. to 300° C. A purge of dry nitrogen at 50 mL/min was maintained over the sample throughout the measurement. The onset of the melting endotherm was reported as the melting point.

Thermogravimetric Analysis (TGA):

TGA thermograms were collected on a TA Instruments Q5000 system, equipped with a 25 position auto-sampler. Typically 1-5 mg of each sample was loaded onto a pre-tared aluminium pan and heated at 10° C./min from 25° C. to 250° C. A nitrogen purge at 25 mL/min was maintained over the sample throughout the measurement.

Dynamic Vapor Sorption (DVS):

DVS data, which was used to determine the hygroscopicity of solids, were collected on a TA Instruments Q5000SA system. The temperature-controlled chamber was set at 25° C. and dry nitrogen was introduced at a flow rate of 10 mL/min. Approximately 1 to 5 mg sample was placed in a semispherical metal-coated quartz crucible or a disposable aluminum pan. A stepwise isotherm experiment at 25° C. was conducted by controlling the relative humidity (RH) in the chamber from 10% to 90%, then down to 10%, at 10% increments to accomplish a full sorption/desorption cycle.

Preparation of the Salt and Co-Crystal Forms of Compound (I)

Example 1—Preparation of Compound (I) Hemisulfate 5 g of Compound (I) free base was dissolved in about 50 mL acetonitrile at about 40° C. 540 mg sulfuric acid was diluted with about 10 mL acetonitrile, and was charged into the Compound (I) solution over about 2.5 h. A slurry was formed during the addition. Afterwards, the slurry was heated to about 70° C. and cooled to about 0° C. over about 2 h. The mixture was filtered, washed with about 10 mL acetonitrile, and dried in the oven at about 50° C. overnight under vacuum. 5.05 g of Compound (I) hemisulfate was obtained.

Example 2—Preparation of Compound (I) Oxalate

A mixture of 100 mg Compound (I) and 19.8 mg oxalic acid was dissolved in acetone and stirred overnight at about room temperature. A slurry was formed and confirmed to be Compound (I) oxalate by XRPD to give the seed batch. A batch was prepared by dissolving 10 g Compound (I) and 2 g oxalic acid in about 50 mL acetone at about 20° C., followed by adding seed crystals from the seed batch. A slurry was formed and about 50 mL n-heptane was charged over about 2 h. The mixture was filtered, washed with 10 mL acetone and dried at about 50° C. under vacuum. 10.7 g of Compound (I) oxalate was obtained.

Example 3—Preparation of Compound (I) Hemiedisylate

A mixture of 100 mg Compound (I) with 24.9 mg ethane-1,2-disulfonic acid dihydrate was mixed in about 1 mL of acetonitrile, tetrahydrofuran, or acetone or a mixture thereof. The mixture was stirred at about room temperature overnight. The slurries were filtered and dried at about 50° C. under vacuum. The solids were examined by XRPD to confirm the formation of Compound (I) hemiedisylate.

Example 4—Preparation of Compound (I) Edisylate

A mixture of 100 mg Compound (I) with 49.8 mg ethane-1,2-disulfonic acid dihydrate was mixed in about 1 mL of acetonitrile, tetrahydrofuran, or acetone or a mixture thereof. When acetonitrile was used, seeding was performed (the seeds came from the experiments using tetrahydrofuran or acetone described in this paragraph). The mixture was stirred at room temperature overnight. The slurries were filtered and dried at about 50° C. under vacuum. The solids were examined by XRPD to confirm the formation of Compound (I) edisylate.

Example 5—Preparation of Compound (I) Heminapadisylate

A mixture of 108.7 mg of Compound (I), 43.1 mg (0.5 eq) of naphthalene-1,5-disulfonic acid, and about 1.5 mL of acetonitrile was sonicated for about 30 minutes in a sealed 4 mL amber glass vial. The sample was agitated by a magnetic stir bar at about 50° C. for about 1 hour, and then cooled to room temperature where the sample remained stirring for about 5 days. The solids were isolated by centrifuge and were dried under vacuum overnight at about 50° C. $^1$H NMR showed about half equivalent naphthalene- 1,5-disulfonic acid and some residual acetonitrile. The sample was further dried at about 125° C.

Example 6—Preparation of Compound (I) Fumarate

A mixture of 100.4 mg of Compound (I), 26.2 mg (1 eq) of fumaric acid, and 0.75 mL of isopropyl acetate was sonicated for about 30 minutes in a sealed 4 mL amber glass vial. The sample was agitated by a magnetic stir bar at about 50° C. for about 1 hour, and then cooled to room temperature where the sample remained stirring for about 2 week. The solids were isolated by centrifuge and were dried under vacuum overnight at about 50° C. $^1$H NMR showed about 1 equivalent fumaric acid.

Another batch was prepared by stirring 500 mg Compound (I) and 127.7 mg (1 eq) fumaric acid in a mixture of 5 mL isopropyl acetate and 0.5 mL water for about 16 hours at about 50° C. and then room temperature for about 2 days. The sample was filtered, washed with 5 mL isopropyl acetate and dried at about 50° C. under vacuum overnight. XRPD analysis of the solids showed the same pattern as the sample in the above experiment.

Example 7—Preparation of Compound (I) Succinate

A mixture of 99.5 mg of Compound (I), 27.1 mg (1 eq) of succinic acid, and 0.75 mL of isopropyl acetate was sonicated for about 30 minutes in a sealed 4 mL amber glass vial. The sample was agitated by a magnetic stir bar at about 50° C. for about 1 hour, and then cooled to room temperature where the sample remained stirring for about 1 week. The solids were isolated by centrifuge and were dried under vacuum overnight at about 50° C. $^1$H NMR showed about 1 equivalent succinic acid.

Another batch was prepared by stirring 500 mg Compound (I) and 129.9 mg (1 eq) succinic acid in 5 mL isopropyl acetate for about three days at room temperature. The sample was filtered, washed with 5 mL isopropyl acetate and dried at about 50° C. under vacuum overnight. XRPD analysis of the solids showed the same pattern as the sample in the above experiment.

What is claimed is:

1. A crystalline hemisulfate, oxalate, hemiedisylate, edisylate, heminapadisylate, fumarate, or succinate of Compound (I):

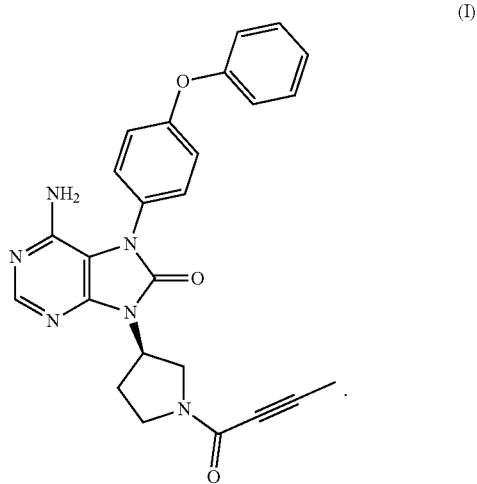 [SMILES: CC#CC(=O)N1CC[C@@H](n2c(=O)n(-c3ccc(Oc4ccccc4)cc3)c3c(N)ncnc32)C1]

(I)

2. The Compound (I) hemisulfate of claim 1 characterized by an X-ray powder diffractogram comprising peaks (±0.2°) at 6.6, 18.6, and 23.7° 2θ as determined on a diffractometer using Cu-Kα radiation.

3. The Compound (I) hemisulfate of claim 2, wherein the diffractogram further comprises peaks at 7.1 and 13.7° 2θ±0.2°.

4. The Compound (I) hemisulfate of claim 3 further characterized by a differential scanning calorimetry curve comprising an endotherm at about 192° C.

5. The Compound (I) oxalate of claim 1 characterized by an X-ray powder diffractogram comprising peaks (±0.2°) at 7.2, 18.2, and 23.3° 2θ as determined on a diffractometer using Cu-Kα radiation.

6. The Compound (I) oxalate of claim 5, wherein the diffractogram further comprises peaks at 13.8 and 20.2° 2θ±0.2°.

7. The Compound (I) oxalate of claim 6 further characterized by a differential scanning calorimetry curve comprising an endotherm at about 171° C.

8. The Compound (I) hemiedisylate of claim 1 characterized by an X-ray powder diffractogram comprising peaks (±0.2°) at 5.9, 11.8, and 17.6° 2θ as determined on a diffractometer using Cu-Kα radiation.

9. The Compound (I) hemiedisylate of claim 8, wherein the diffractogram further comprises peaks at 21.2 and 23.6° 2θ±0.2°.

10. The Compound (I) hemiedisylate of claim 9 further characterized by a differential scanning calorimetry curve comprising an endotherm at about 165° C.

11. The Compound (I) edisylate of claim 1 characterized by an X-ray powder diffractogram comprising peaks (±0.2°) at 5.7, 16.6, and 24.2° 2θ as determined on a diffractometer using Cu-Kα radiation.

12. The Compound (I) edisylate of claim 11, wherein the diffractogram further comprises peaks at 11.1 and 22.2° 2θ±0.2°.

13. The Compound (I) edisylate of claim 12 further characterized by a differential scanning calorimetry curve comprising an endotherm at about 154° C.

14. The Compound (I) heminapadisylate of claim 1 characterized by an X-ray powder diffractogram comprising peaks (±0.2°) at 15.5, 16.5, and 23.8° 2θ as determined on a diffractometer using Cu-Kα radiation.

15. The Compound (I) heminapadisylate of claim 14, wherein the diffractogram further comprises peaks at 5.6 and 20.3° 2θ±0.2°.

16. The Compound (I) heminapadisylate of claim 15 further characterized by a differential scanning calorimetry curve comprising an endotherm at about 180° C.

17. The Compound (I) fumarate of claim 1 characterized by an X-ray powder diffractogram comprising peaks (±0.2°) at 13.0, 16.6, and 19.9° 2θ as determined on a diffractometer using Cu-Kα radiation.

18. The Compound (I) fumarate of claim 17, wherein the diffractogram further comprises peaks at 8.3 and 19.0° 2θ±0.2°.

19. The Compound (I) fumarate of claim 18 further characterized by a differential scanning calorimetry curve comprising an endotherm at about 158° C.

20. The Compound (I) succinate of claim 1 characterized by an X-ray powder diffractogram comprising peaks (±0.2°) at 13.2, 16.5, and 18.0° 2θ as determined on a diffractometer using Cu-Kα radiation.

21. The Compound (I) succinate of claim 20, wherein the diffractogram further comprises peaks at 8.2 and 18.6° 2θ±0.2°.

22. The Compound (I) succinate of claim 21 further characterized by a differential scanning calorimetry curve comprising an endotherm at about 142° C.

23. A pharmaceutical composition comprising a pharmaceutically acceptable carrier, and one or more compounds of claim 1.

24. A kit comprising the compound of claim 1, or a label and/or instructions for use.

25. A process for making a crystalline hemisulfate, oxalate, hemiedisylate, edisylate, heminapadisylate, fumarate, or succinate of Compound (I):

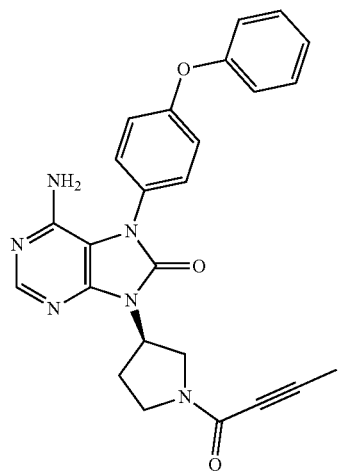

(I)

wherein the process comprises the steps of:
combining Compound (I) and sulfuric acid, oxalic acid, ethane-1,2-disulfonic acid, naphthalene-1,5-disulfonic acid, fumaric acid or succinic acid in a suitable solvent to obtain a mixture; and
collecting the crystalline hemisulfate, oxalate, hemiedisylate, edisylate, heminapadisylate, fumarate, or succinate of Compound (I).

26. The process of claim 25, wherein the process comprises the steps of:
i) combining Compound (I) and sulfuric acid in a suitable solvent to obtain a mixture;
ii) heating the mixture obtained in step i) to about 70° C.;
iii) cooling the mixture obtained in step ii) to about 0° C.; and
iv) collecting the solid material obtained in step iii) to obtain the hemisulfate of Compound (I).

27. The process of claim 25, wherein the process comprises the steps of:
i) dissolving Compound (I) and oxalic acid in a suitable solvent at room temperature to obtain a mixture; and
ii) collecting the solid material obtained in step i) to obtain the oxalate of Compound (I).

28. The process of claim 25, wherein the process comprises the steps of:
i) combining Compound (I) and ethane-1,2-disulfonic acid dihydrate in a suitable solvent at room temperature to obtain a mixture; and
ii) collecting the solid material obtained in step i) to obtain the hemiedisylate of Compound (I).

29. The process of claim 25, wherein the process comprises the steps of:
i) combining Compound (I) and ethane-1,2-disulfonic acid dihydrate in a suitable solvent at room temperature to obtain a mixture; and
ii) collecting the solid material obtained in step i) to obtain the edisylate of Compound (I).

30. The process of claim 25, wherein the process comprises the steps of:
i) combining Compound (I) and naphthalene-1,5-disulfonic acid in a suitable solvent to obtain a mixture;
ii) heating the mixture obtained in step i) to about 50° C.;
iii) cooling the mixture obtained in step ii) to room temperature; and
iv) collecting the solid material obtained in step iii) to obtain the heminapadisylate of Compound (I).

31. The process of claim 25, wherein the process comprises the steps of:
i) combining Compound (I) and fumaric acid in a suitable solvent;
ii) heating the mixture obtained in step i) to about 50° C.;
iii) cooling the mixture obtained in step ii) to room temperature; and
iv) collecting the solid material obtained in step iii) to obtain the fumarate of Compound (I).

32. The process of claim 25, wherein the process comprises the steps of:
i) combining Compound (I) and succinic acid in a suitable solvent;
ii) heating the mixture obtained in step i) to about 50° C.;
iii) cooling the mixture obtained in step ii) to room temperature; and
iv) collecting the solid material obtained in step iii) to obtain the succinate of Compound (I).

* * * * *